United States Patent
Orr et al.

(10) Patent No.: US 11,169,621 B2
(45) Date of Patent: Nov. 9, 2021

(54) ASSESSING POSTURAL SWAY IN VIRTUAL OR AUGMENTED REALITY

(71) Applicant: XR Health IL LTD, Tel Aviv (IL)

(72) Inventors: Eran Orr, Brookline, MA (US); Tal Arbel, Hod-Hasharon (IL); Aryeh Efergan, Beer-Sheva (IL); Omer Weissberger, Even-Yehuda (IL)

(73) Assignee: XR Health IL LTD, Tel Aviv (IL)

( * ) Notice: Subject to any disclaimer, the term of this patent is extended or adjusted under 35 U.S.C. 154(b) by 28 days.

(21) Appl. No.: 16/779,004

(22) Filed: Jan. 31, 2020

(65) Prior Publication Data
US 2020/0167009 A1    May 28, 2020

Related U.S. Application Data

(63) Continuation of application No. PCT/US2018/045035, filed on Aug. 2, 2018.

(51) Int. Cl.
| | | |
|---|---|---|
| *G06F 3/0346* | (2013.01) | |
| *G02B 27/01* | (2006.01) | |
| *G06F 3/01* | (2006.01) | |
| *G06F 3/0481* | (2013.01) | |

(52) U.S. Cl.
CPC ......... *G06F 3/0346* (2013.01); *G02B 27/017* (2013.01); *G06F 3/014* (2013.01); *G06F 3/04815* (2013.01)

(58) Field of Classification Search
CPC .... G06F 3/0346; G06F 3/014; G06F 3/04815; G06F 3/01; G02B 27/017; G02B 27/01
See application file for complete search history.

(56) References Cited

U.S. PATENT DOCUMENTS

| | | | |
|---|---|---|---|
| 8,979,665 B1* | 3/2015 | Najafi | A63B 69/3608 |
| | | | 473/269 |
| 2010/0268125 A9 | 10/2010 | Epley | |
| 2012/0108909 A1* | 5/2012 | Slobounov | G16H 50/30 |
| | | | 600/300 |

(Continued)

FOREIGN PATENT DOCUMENTS

WO    WO-2019/028268 A1    2/2019

OTHER PUBLICATIONS

Keshner "Posture and Spatial Orientation Driven by Virtual Reality" Stud Health Technol Inform. 2009 (Year: 2009).*

(Continued)

*Primary Examiner* — Amit Chatly
(74) *Attorney, Agent, or Firm* — Foley Hoag LLP; Erik A. Huestis

(57) ABSTRACT

A virtual or augmented reality based tracking system for assessment of postural sway is provided. In various embodiments, positional data are collected from a user from a headset and/or one or more hand sensors. The positional data is processed to determine the center of mass of the user. In determining of the center of mass, positional data may be given a higher or lower weight compared to other positional data. A virtual reality environment is presented to the user through the headset and may be altered to simulate unbalancing of the user. The raw position data and center of mass are sent to a remote server. A report of user sway is generated from the center of mass. Nausea reduction may be implemented by narrowing a field of vision of the user.

18 Claims, 44 Drawing Sheets

100

(56) References Cited

U.S. PATENT DOCUMENTS

2016/0007935 A1* 1/2016 Hernandez .......... A61B 5/6814
600/301
2016/0154241 A1* 6/2016 Alhashim ............... A63F 13/24
345/8

OTHER PUBLICATIONS

International Search Report and Written Opinion for International Application No. PCT/US2018/045035 dated Oct. 4, 2018.
Keshner et al., "Postural and Spatial Orientation Driven by Virtual Reality," Stud Health Technol Inform, 145:209-228 (2009).

* cited by examiner

Patient 1

HMD

| Measure | R | P |
|---|---|---|
| Sway Index | 0.985251 | 5.16E-23 |
| Tot displacement | 0.982669 | 4.86E-22 |
| CoP mean Velocity | 0.982688 | 4.79E-22 |
| Ellipse Radius 1 | 0.979845 | 3.95E-21 |
| Ellipse Radius 2 | 0.982677 | 4.83E-22 |
| Ellipse area | 0.983311 | 2.88E-22 |

HMD_HANDS

| Measure | R | P |
|---|---|---|
| Sway Index | 0.524625 | 0.002917917 |
| Tot displacement | 0.668378 | 5.42E-05 |
| CoP mean Velocity | 0.668185 | 5.46E-05 |
| Ellipse Radius 1 | 0.901334 | 1.10E-11 |
| Ellipse Radius 2 | 0.419736 | 0.02093752 |
| Ellipse area | 0.480282 | 0.007227511 |

HMD_HANDS_weighted

| Measure | R | P |
|---|---|---|
| Sway Index | 0.629232791 | 0.000195 |
| Tot displacement | 0.777318169 | 4.36E-07 |
| CoP mean Velocity | 0.777174912 | 4.39E-07 |
| Ellipse Radius 1 | 0.932839672 | 6.15E-14 |
| Ellipse Radius 2 | 0.597024736 | 0.000496 |
| Ellipse area | 0.729711 | 4.75E-06 |

Fig. 6

Patient 2

HMD

| Measure | R | P |
|---|---|---|
| Sway Index | 0.970710 | 7.00E-19 |
| Tot displacement | 0.935322 | 3.69E-14 |
| CoP mean Velocity | 0.935670 | 3.43E-14 |
| Ellipse Radius 1 | 0.965182 | 7.61E-18 |
| Ellipse Radius 2 | 0.969589 | 1.18E-18 |
| Ellipse area | 0.969689 | 1.12E-18 |

HMD_HANDS

| Measure | R | P |
|---|---|---|
| Sway Index | -0.7346 | 3.80E-06 |
| Tot displacement | 0.942244 | 7.89E-15 |
| CoP mean Velocity | 0.942244 | 7.89E-15 |
| Ellipse Radius 1 | 0.982023 | 8.08E-22 |
| Ellipse Radius 2 | 0.982897 | 4.04E-22 |
| Ellipse area | 0.980495 | 2.51E-21 |

HMD_HANDS_weighted

| Measure | R | P |
|---|---|---|
| Sway Index | 0.981183 | 1.52E-21 |
| Tot displacement | 0.944628 | 4.44E-15 |
| CoP mean Velocity | 0.944628 | 4.44E-15 |
| Ellipse Radius 1 | 0.983551 | 2.35E-22 |
| Ellipse Radius 2 | 0.980893 | 1.88E-21 |
| Ellipse area | 0.980477 | 2.54E-21 |

Fig. 7

ASSESSING POSTURAL SWAY IN VIRTUAL OR AUGMENTED REALITY

CROSS-REFERENCE TO RELATED APPLICATIONS

This application is a continuation of International Application No. PCT/US2018/045035, filed Aug. 2, 2018, which claims the benefit of U.S. Provisional Application No. 62/540,413, filed Aug. 2, 2017, each of which is hereby incorporated by reference herein in its entirety.

BACKGROUND

Embodiments of the present disclosure relate to physical therapy using virtual or augmented reality, and more specifically, to assessing postural sway in virtual or augmented reality environments.

Postural stability is an integral component of the motor control and coordination process of the body, which is required for preserving steadiness during static and dynamic activities. Postural stability relies on proprioceptive afferents and complex sensorimotor actions, and is mediated by both higher, controlled, and lower, automatic, levels of processing in the brain. This implies the involvement of basal ganglia—cortical loop for higher level processing and brainstem synergies for lower level processing. Any impairment to these proprioceptive afferents and complex sensorimotor actions within the body may cause a person to lose their postural stability and, thus, be at risk for injury, e.g., falling.

BRIEF SUMMARY

According to embodiments of the present disclosure, methods of and computer program products for postural sway assessment are provided. In various embodiments, a virtual environment may be provided to a user via a virtual or augmented reality system and the virtual reality system may include a head-mounted display. Positional information of the user may be collected, wherein collecting positional information includes collecting positional information of the head-mounted display. A center of mass of the user may be determined from the positional information. A user sway metric may be determined from the center of mass.

In various embodiments, collecting positional information includes collecting positional information of a first hand sensor. In various embodiments, collecting positional information includes collecting positional information of a second hand sensor. In various embodiments, the method further includes altering the virtual environment to simulate an unbalancing of the user. In various embodiments, altering the environment comprises moving a horizon in a predetermined direction. In various embodiments, the method further includes narrowing a field of vision of the user while altering the environment. In various embodiments, determining the user sway metric includes computing a standard deviation of an average deviation of the center of mass from a predetermined baseline. In various embodiments, determining the user sway metric includes assigning a first weight to positional information of the head mounted display, assigning a second weight to positional information of the first hand sensor, and assigning a third weight to positional information of the second hand sensor. In various embodiments, the first weight, the second weight, and the third weight are equal. In various embodiments, the first weight, the second weight, and the third weight are different. In various embodiments, the first weight is greater than the second weight and the third weight. In various embodiments, the second weight and the third weight are equal.

In various embodiments, a system includes a virtual or augmented reality display adapted to display a virtual environment to a user and the virtual reality display may include a head-mounted display and a computing node comprising a computer readable storage medium having program instructions embodied therewith. The program instructions may be executable by a processor of the computing node to cause the processor to perform a method including: collecting positional information of the user, wherein collecting positional information includes collecting positional information of the head-mounted display; determining a center of mass of the user from the positional information; and determining a user sway metric from the center of mass.

In various embodiments, collecting positional information comprises collecting positional information of a first hand sensor. In various embodiments, collecting positional information includes collecting positional information of a second hand sensor. In various embodiments, the program instructions further executable by the processor to alter the virtual environment to simulate an unbalancing of the user. In various embodiments, altering the environment comprises moving a horizon in a predetermined direction. In various embodiments, the program instructions are further executable by the processor to narrow a field of vision of the user while altering the environment. In various embodiments, determining the user sway metric comprises computing a standard deviation of an average deviation of the center of mass from a predetermined baseline. In various embodiments, determining the user sway metric comprises assigning a first weight to positional information of the head mounted display, assigning a second weight to positional information of the first hand sensor, and assigning a third weight to positional information of the second hand sensor. In various embodiments, the first weight, the second weight, and the third weight are equal. In various embodiments, the first weight, the second weight, and the third weight are different. In various embodiments, the first weight is greater than the second weight and the third weight. In various embodiments, the second weight and the third weight are equal.

In various embodiments, a computer program product for assessing postural sway includes a computer readable storage medium having program instructions embodied therewith. The program instructions may be executable by a processor to cause the processor to perform a method including: collecting positional information of a user, wherein collecting positional information includes collecting positional information of the head-mounted display; determining a center of mass of the user from the positional information; and determining a user sway metric from the center of mass.

In various embodiments, collecting positional information comprises collecting positional information of a first hand sensor. In various embodiments, collecting positional information comprises collecting positional information of a second hand sensor. In various embodiments, the program instructions are further executable by the processor to alter the virtual environment to simulate an unbalancing of the user. In various embodiments, altering the environment includes moving a horizon in a predetermined direction. In various embodiments, the program instructions are further executable by the processor to narrow a field of vision of the user while altering the environment. In various embodiments, determining the user sway metric comprises computing a standard deviation of an average deviation of the center of mass from a predetermined baseline. In various embodiments, determining the user sway metric comprises assigning a first weight to positional information of the head mounted display, assigning a second weight to positional information of the first hand sensor, and assigning a third weight to positional information of the second hand sensor. In various embodiments, the first weight, the second weight, and the third weight are equal. In various embodiments, the first weight, the second weight, and the third weight are different. In various embodiments, the first weight is greater than the second weight and the third weight. In various embodiments, the second weight and the third weight are equal.

BRIEF DESCRIPTION OF THE SEVERAL VIEWS OF THE DRAWINGS

FIGS. 6 and 7 show tables of Pearson correlation coefficients for a first and second patient, respectively, according to embodiments of the present disclosure.

DETAILED DESCRIPTION

Figure 1:
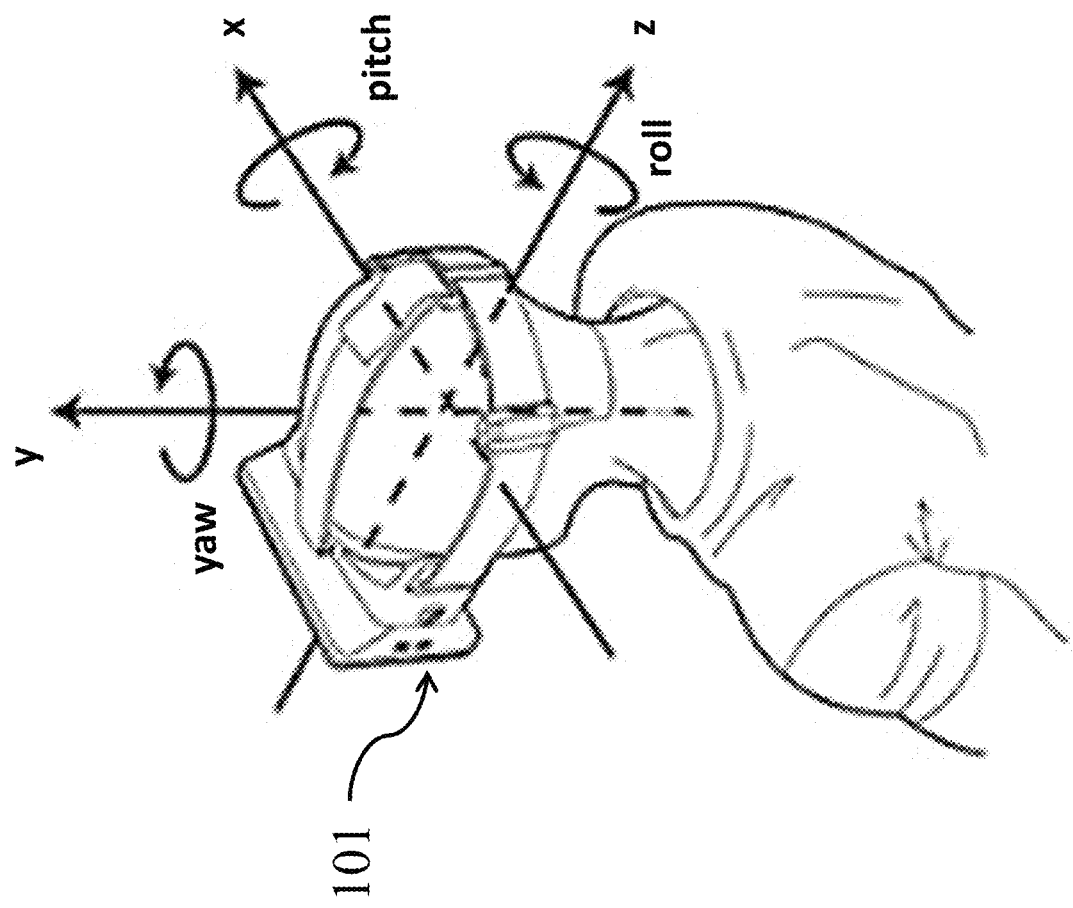
FIG. 1 illustrates an exemplary virtual reality headset according to embodiments of the present disclosure.

Physical therapy attempts to address the illnesses or injuries that limit a person's abilities to move and perform functional activities in their daily lives. Physical therapy may be prescribed to address a variety of pain and mobility issues across various regions of the body. In general, a program of physical therapy is based on an individual's history and the results of a physical examination to arrive at a diagnosis. A given physical therapy program may integrate assistance with specific exercises, manual therapy and manipulation, mechanical devices such as traction, education, physical agents such as heat, cold, electricity, sound waves, radiation, assistive devices, prostheses, orthoses and other interventions. Physical therapy may also be prescribed as a preventative measure to prevent the loss of mobility before it occurs by developing fitness and wellness-oriented programs for healthier and more active lifestyles. This may include providing therapeutic treatment where movement and function are threatened by aging, injury, disease or environmental factors.

As an example, individuals suffer from neck pain or need to perform neck exercises for various reasons. For example, people who have been involved in a motor vehicle accident or have suffered an injury while playing contact sports are prone to develop a whiplash associated disorder (WAD), a condition resulting from cervical acceleration-deceleration (CAD). It will be appreciated that this is just one of many potential injuries that may result in neck injury or pain necessitating rehabilitation.

The majority of people who suffer from non-specific neck pain (NSNP) may have experienced symptoms associated with WAD or have an undiagnosed cervical herniated disc. For this population, the recommended treatment regimen often includes a variety of exercises promoting neck movement and other functional activity training, leading to improved rehabilitation.

Poor adherence to treatment can have negative effects on outcomes and healthcare cost, irrespective of the region of the body affected. Poor treatment adherence is associated with low levels of physical activity at baseline or in previous weeks, low in-treatment adherence with exercise, low self-efficacy, depression, anxiety, helplessness, poor social support/activity, greater perceived number of barriers to exercise and increased pain levels during exercise. Studies have shown that about 14% of physiotherapy patients do not return for follow-up outpatient appointments. Other studies have suggested that overall non-adherence with treatment and exercise performance may be as high as 70%. Patients that suffer from chronic or other long-term conditions (such as those associated with WAD or NSNP) are even less inclined to perform recommended home training.

Adherent patients generally have better treatment outcomes than non-adherent patients. However, although many physical therapy exercises may be carried out in the comfort of one's home, patients cite the monotony of exercises and associated pain as contributing to non-adherence.

Irrespective of adherence, home training has several limitations. With no direct guidance from the clinician, the patient has no immediate feedback to confirm correct performance of required exercises. Lack of such guidance and supervision often leads to even lower adherence. As a result, the pain of an initial sensed condition may persist or even worsen—leading to other required medical interventions that could have been prevented, thus also increasing associated costs of the initial condition.

Accordingly, there is a need for devices, systems, and methods that facilitate comprehensive performance and compliance with physical therapy and therapeutic exercise regimens.

According to various embodiments of the present disclosure, various devices, systems, and methods are provided to facilitate therapy and physical training assisted by virtual or augmented reality environments.

It will be appreciated that a variety of virtual and augmented reality devices are known in the art. For example, various head-mounted displays providing either immersive video or video overlay are provided by various vendors. Some such devices integrate a smart phone within a headset, the smart phone providing computing and wireless communication resources for each virtual or augmented reality application. Some such devices connect via wired or wireless connection to an external computing node such as a personal computer. Yet other devices may include an integrated computing node, providing some or all of the computing and connectivity required for a given application.

Virtual or augmented reality displays may be coupled with a variety of motion sensors in order to track a user's motion within a virtual environment. Such motion tracking may be used to navigate within a virtual environment, to manipulate a user's avatar in the virtual environment, or to interact with other objects in the virtual environment. In some devices that integrate a smartphone, head tracking may be provided by sensors integrated in the smartphone, such as an orientation sensor, gyroscope, accelerometer, or geomagnetic field sensor. Sensors may be integrated in a headset, or may be held by a user, or attached to various body parts to provide detailed information on user positioning.

It will also be appreciated that various embodiment are applicable to virtual and augmented reality environments in general, including those that are presented without a headset. For example, a magic window implementation of VR or AR uses the display on a handheld device such as a phone as a window into a virtual space. By moving the handheld device, by swiping, or by otherwise interacting with the handheld device, the user shifts the field of view of the screen within the virtual environment. A center of a user's field of view can be determined based on the orientation of the virtual window within the virtual space without the need for eye-tracking. However, in devices including eye-tracking, more precision may be obtained.

An aspect of various physical therapies is the process of sway assessment. Conventional approaches to sway assessment are limited by the need for an approachable measurement device, the need to measure change in center of mass via the change of weight on feet using a platter, and inability to change scenery.

To address these and other limitations of conventional approaches, the present disclosure provides for measurement of sway in virtual or augmented reality. In particular, the present disclosure provide for calculating sway based on sensor feedback from handheld (or otherwise hand-affixed) sensors and from head mounted sensors. Using this sensor input, a test is provided that changes scenery in order to manipulate the visual & vestibular systems in order to get a comprehensive result.

Postural sway, in terms of human sense of balance, refers to horizontal movement around the center of mass. Sway can be a part of various test protocols, including: Fall risk; Athletic single leg stability; Limits of stability; or Postural stability.

Measurements of postural sway can provide accurate fall risk assessment and conditioning for adults, and neuromuscular control assessment, by quantifying the ability to maintain static or dynamic bilateral and unilateral postural stability on a static or dynamic surface.

Various clinical tests for balance may quantify balance in terms of various indices. A stability index may measure the average position from center. This measure does not indicate how much sway occurred during the test, but rather the position alone. A sway index may measure the standard deviation of the stability index over time. The higher the sway index, the more unsteady a subject was during the test. This provides an objective quantification of sway. For example, a pass/fail result of a test may be determined based on the sway index over a predetermined time period, such as 30 seconds. Likewise, a scale may be applied to the sway index, for example a value of 1 to 4 to characterize the sway where 1 corresponds to minimal sway, 4=a fall. Similarly, a color scale may be applied to the sway index, for example, a green color may indicate minimal sway, a yellow color may indicate moderate sway, and a red color may indicate significant sway or a fall.

Various advantages of using virtual or augmented reality as set out herein for assessing postural sway will be apparent. For example, center of mass assessment is improved over conventional approaches that rely on measuring the changes of weight on feet on a single platter. The actual average center of mass of a standing human being is generally at the Sacrum-2 point. This more precise center of mass point can be assessed and measured continuously using hand sensors and a head mounted display sensor in accordance with the present disclosure. These data are evaluated against posture guidelines provided in the VR/AR environment to provide a continuous index for center of mass. As set out below, such a continuous index may be generated at a rate of up to about 150 Hz.

In various embodiments, a patient's balance may be challenged through a change of scenery or environment. This allows better control over a user input than conventional approaches that rely on separately limiting visual, vestibular, and somatosensory feedback. For example, eyes may be closed to neutralize vision. A subject may stand on high density foam cushion to neutralize the somatosensory system. A subject may be placed in a visual conflict dome in order to neutralize the vestibular system.

With reference now to FIG. 1, an exemplary virtual reality headset is illustrated according to embodiments of the present disclosure. In various embodiments, system 100 is used to collected data from motion sensors including hand sensors (not pictured), sensors included in headset 101, and additional sensors such as torso sensors or a stereo camera. In some embodiments, data from these sensors is collected at a rate of up to about 150 Hz. As pictured, data may be collected in six degrees of freedom: X—left/right; Y—up/down/height; Z—foreword/backward; P—pitch; R—roll; Y—yaw.

Figure 2:
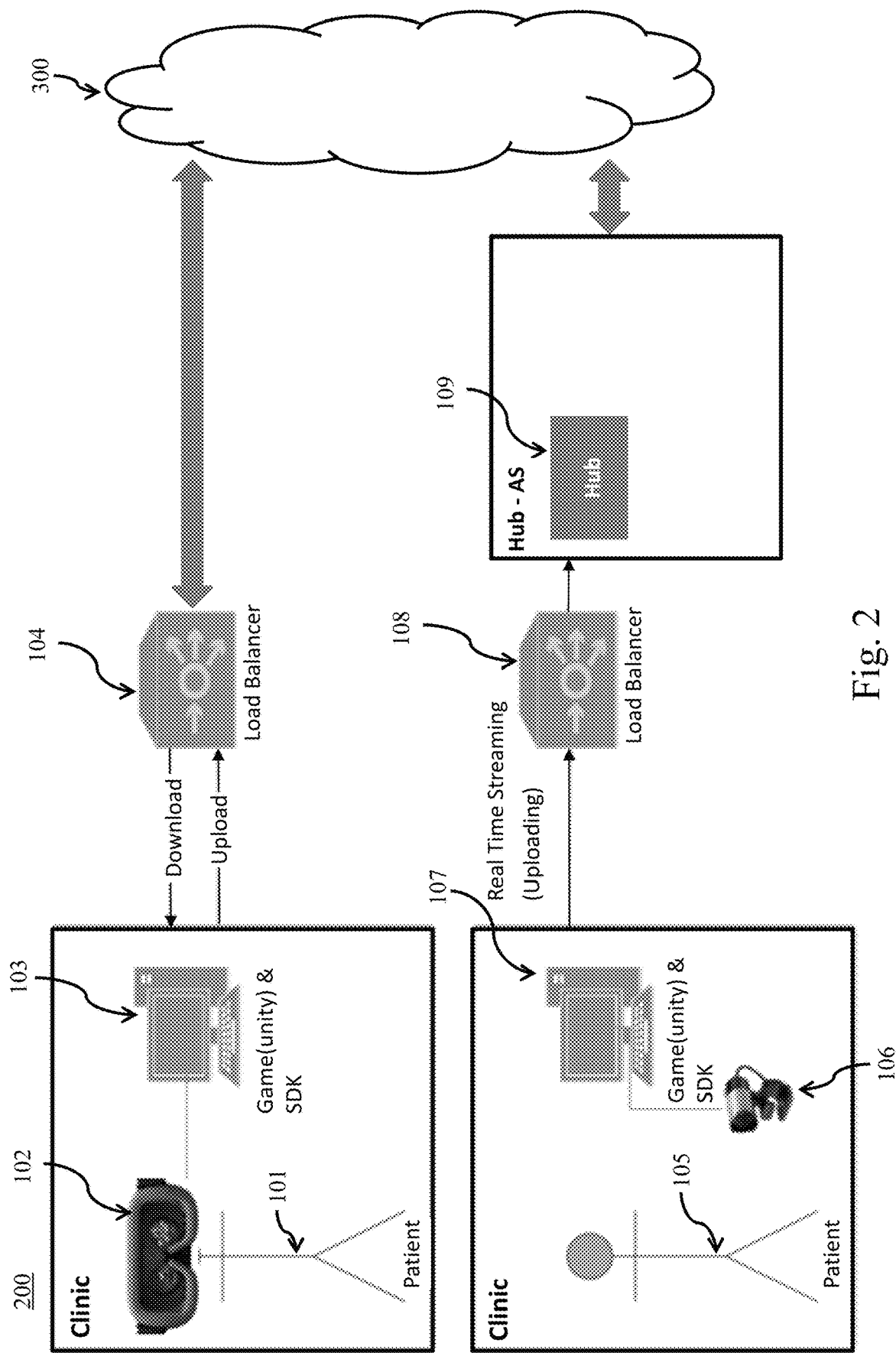
FIG. 2 illustrates an exemplary system according to embodiments of the present disclosure.

Referring to FIG. 2, an exemplary system according to embodiments of the present disclosure is illustrated. Data is gather from user 101 by wearable 102. In some embodiments, computing node 103 is connected to wearable 102 by wired or wireless connection. In some embodiments, computing node 103 is integrated in wearable 102. In some embodiments, a load balancer 104 receives data from computing node 103 via a network, and divides the data among multiple cloud resources 300.

In some embodiments, camera 106 observes user 105. Video is provided to computing node 107, which in turn sends the video data via a network. In some embodiments, load balancer 108 receives data from computing node 107 via a network, and divides the data among multiple cloud resources 300. In some embodiments, hub 109 receives data from computing node 107 and stores or relays incoming video and event information for further processing.

Figure 3:
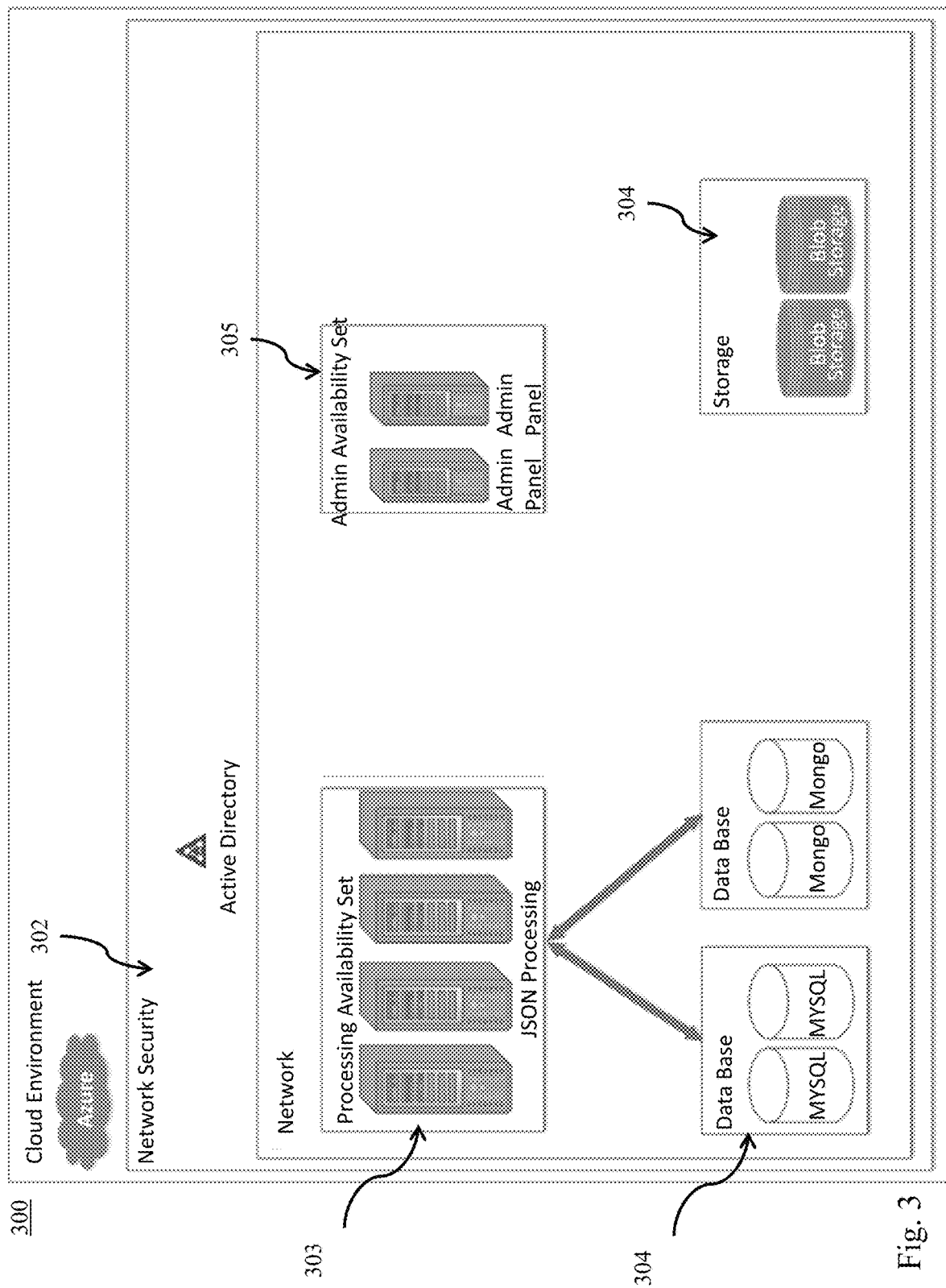
FIG. 3 illustrates an exemplary cloud service according to embodiments of the present disclosure.

Referring to FIG. 3, an exemplary cloud environment according to embodiments of the present disclosure is illustrated. Various cloud platforms are suitable for use according to the present disclosure. A network security layer 302 applies security policy and rules with respect to service access. In some embodiments, Active Directory or equivalent directory services may be used for user authentication.

A set of processing servers 303 are responsible for receiving and analyzing data from the various user devices described herein. In various embodiments, processing servers 303 are also responsible for sending data, such as history information, to users upon request. The number of processing servers may be scaled to provide a desired level of redundancy and performance.

Processing servers 303 are connected to datastores 304. Datastores 304 may include multiple database types. For example, a SQL database such as MySQL may be used to maintain patient or doctor details, or user credentials. A NoSQL database such as MongoDB may be used to store large data files. Datastores 304 may be backed by storage 305.

In some embodiments, admin servers 306 provide a remotely accessible user interface, such as a web interface, for administering users and data of the system. The number of admin servers may be scaled to provide a desired level of redundancy and performance.

Figure 4:
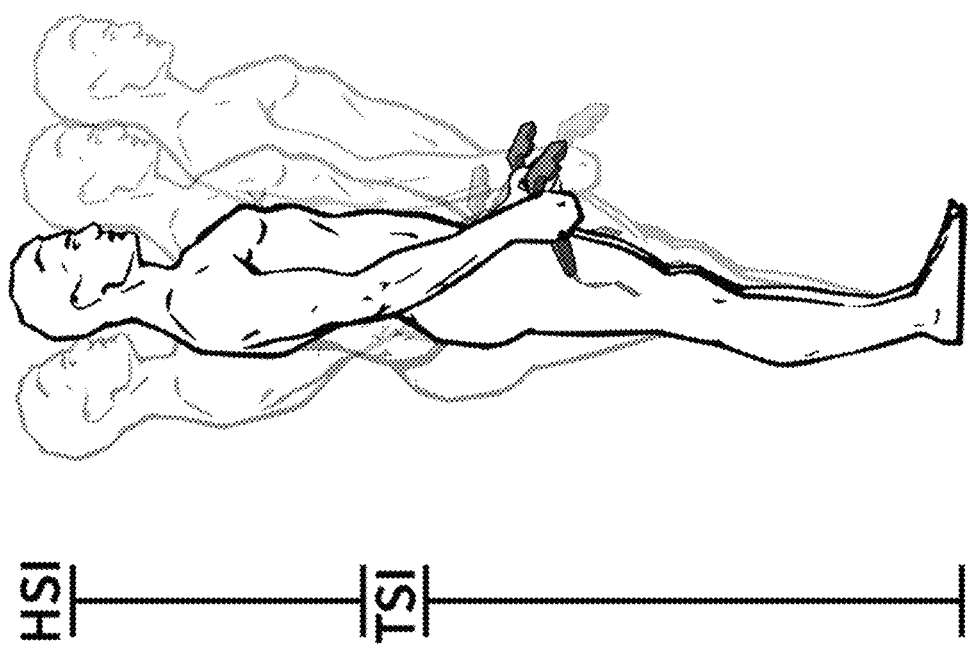
FIG. 4 illustrates the Torso Sway Index (TSI) and Head Sway Index (HSI) of a person.

Referring now to FIG. 4, the Torso Sway Index (TSI) and Head Sway Index (HSI) of a person are illustrated. As set out herein, these indices, alone or in combination provide improves assessment of fall risk and postural stability, both static and dynamic.

Figure 5:
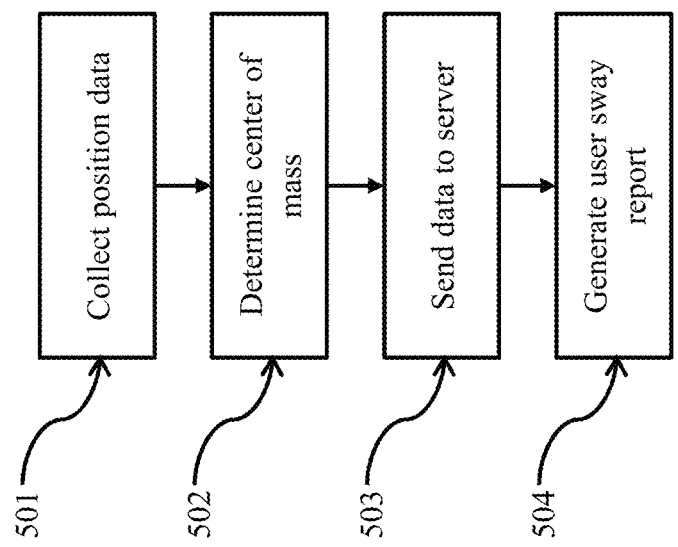
FIG. 5 illustrates a method of sway assessment according to embodiments of the present disclosure.
Figure 8A:
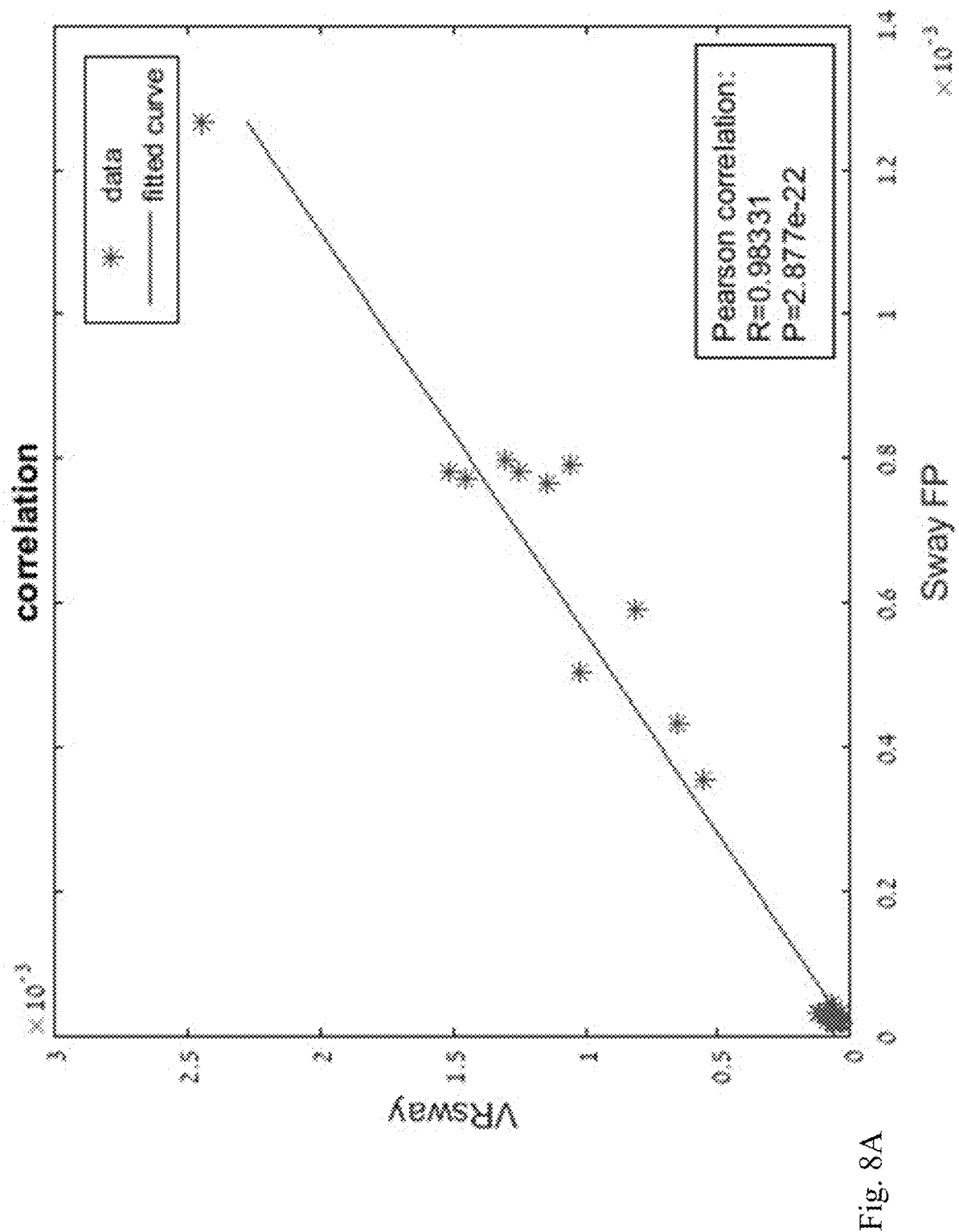
FIGS. 8A-8F show graphs of Pearson correlations of VR and force plate methods for a first patient according to an embodiment of the present disclosure.
Figure 8B:
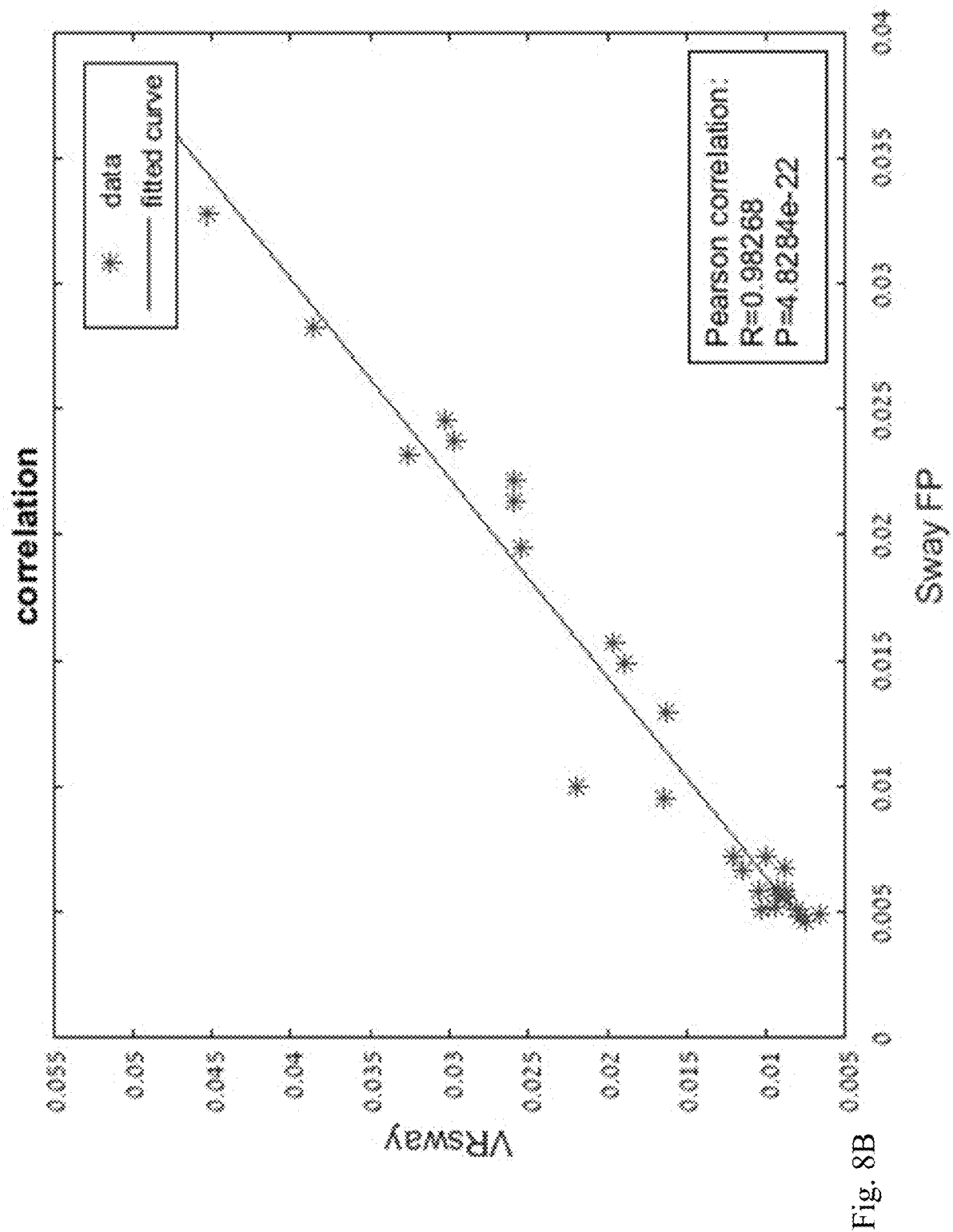
Figure 8C:
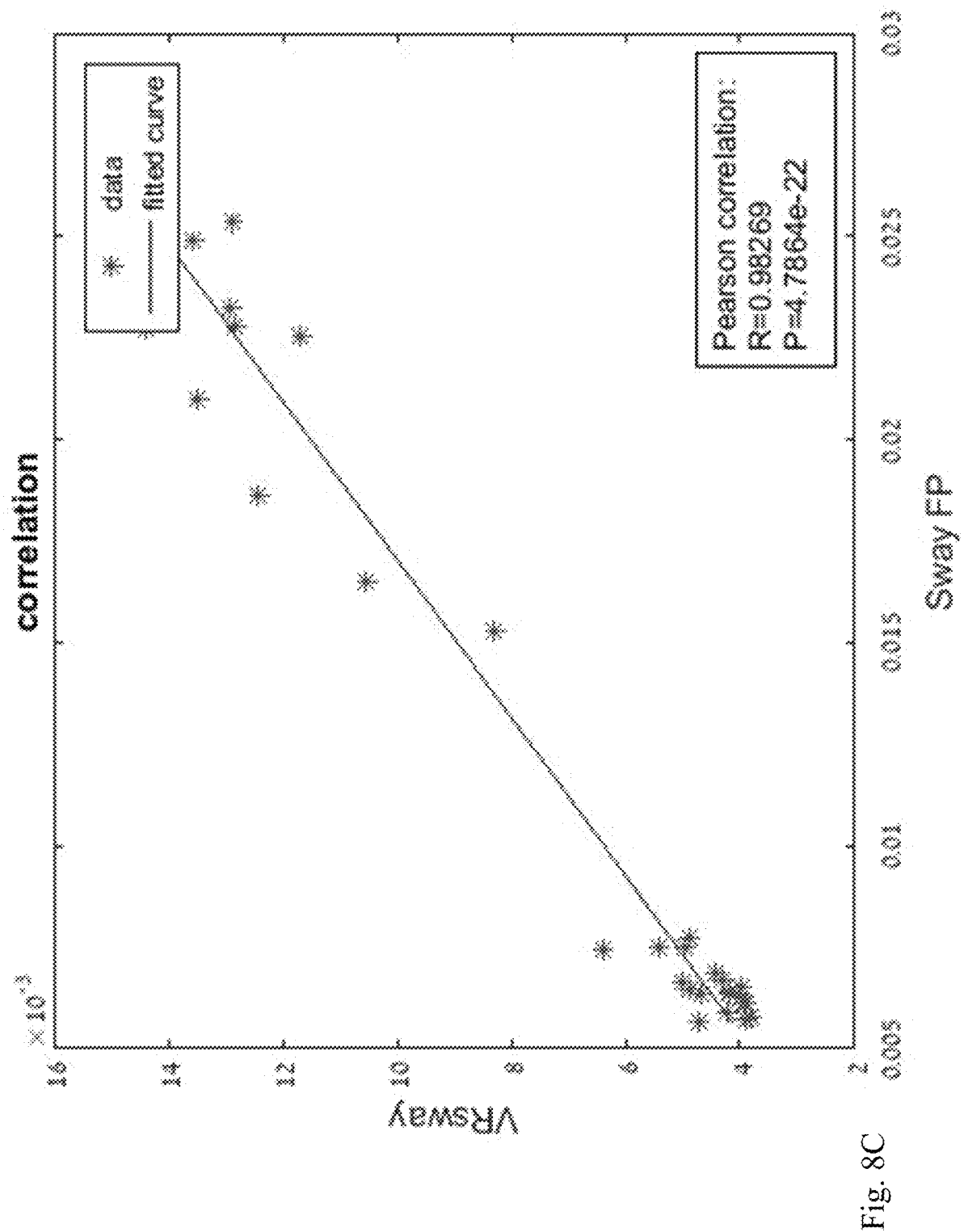
Figure 8D:
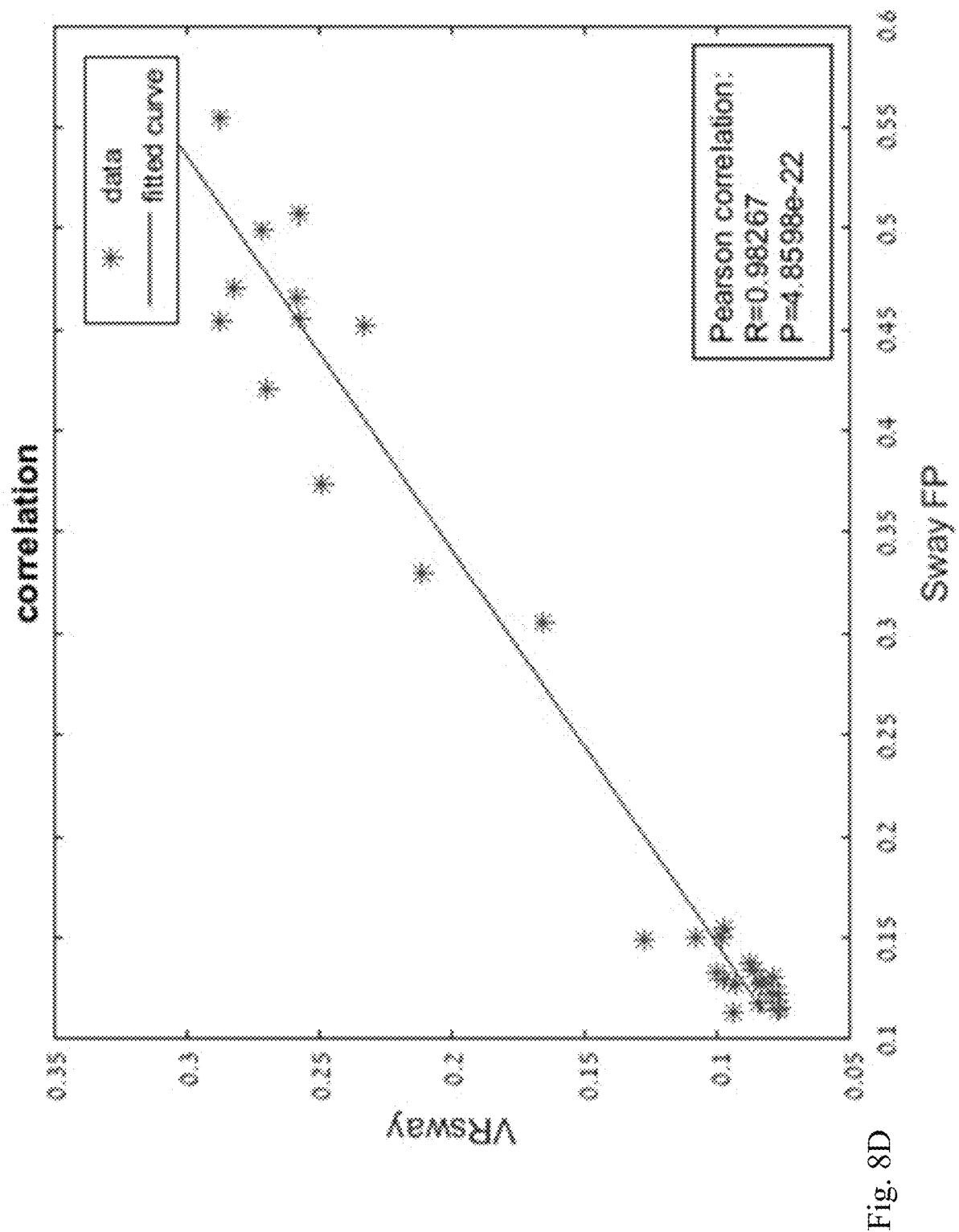
Figure 8E:
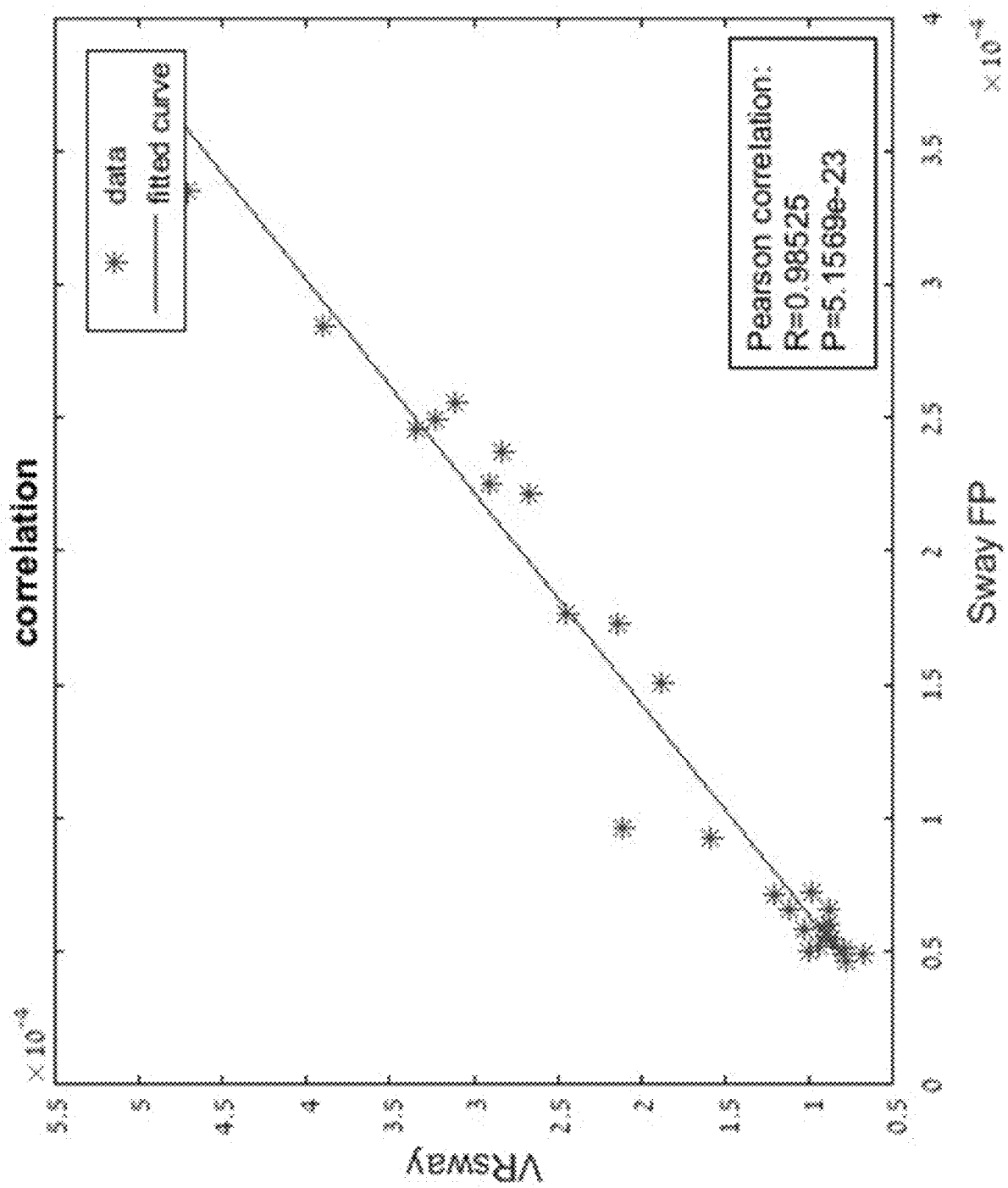
Figure 8F:
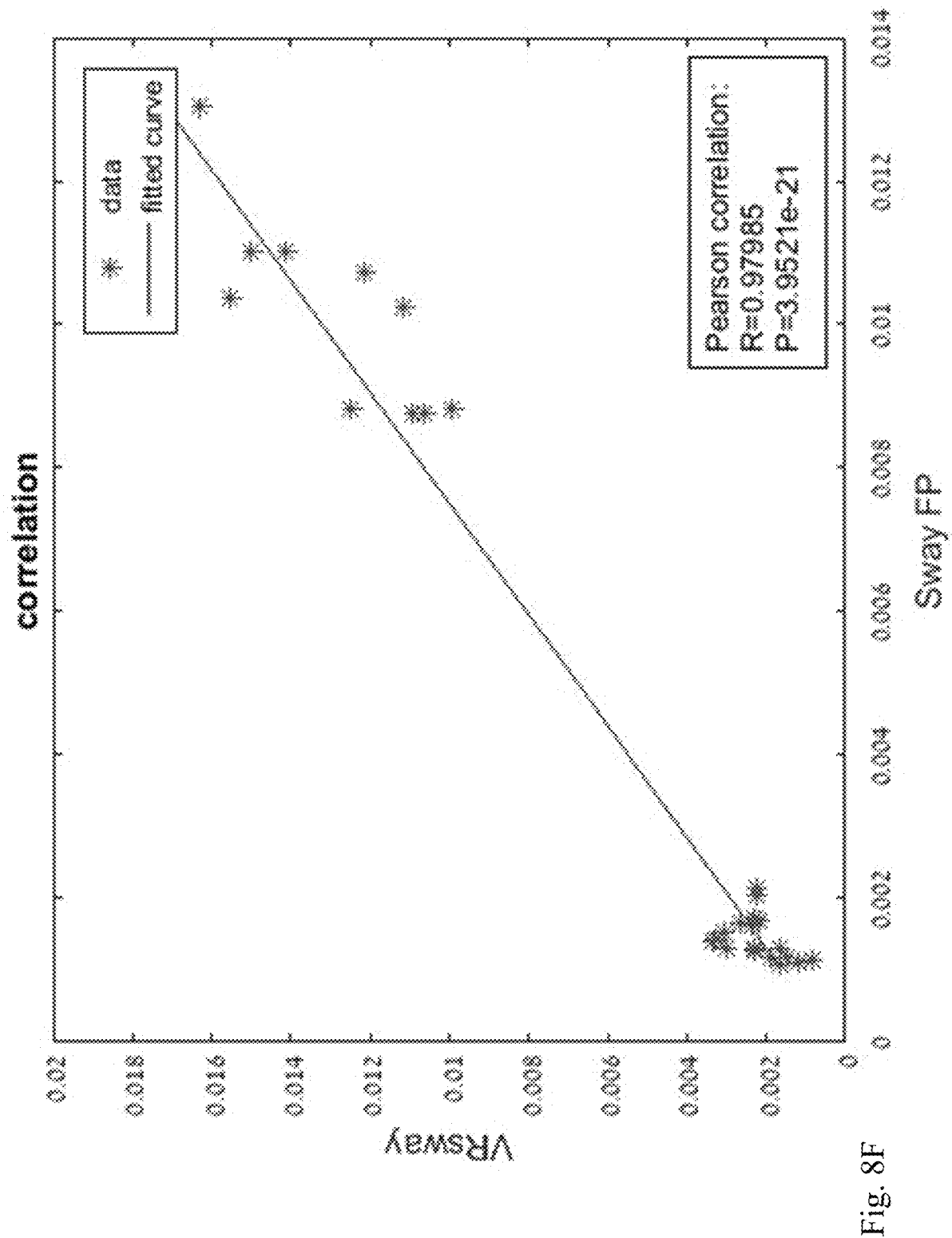
Figure 9A:
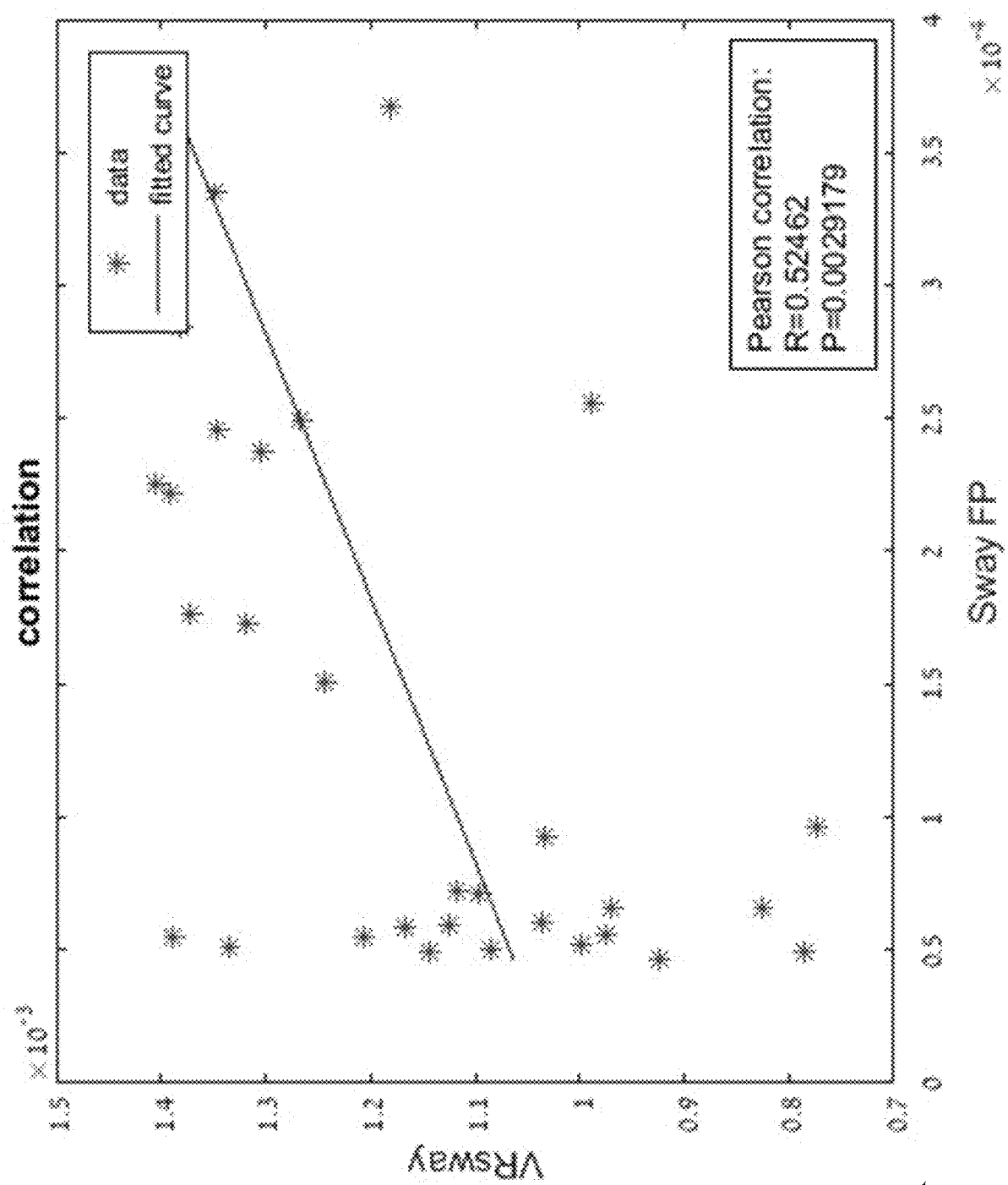
FIGS. 9A-9F show graphs of Pearson correlations of VR and force plate methods for a first patient according to an embodiment of the present disclosure.
Figure 9B:
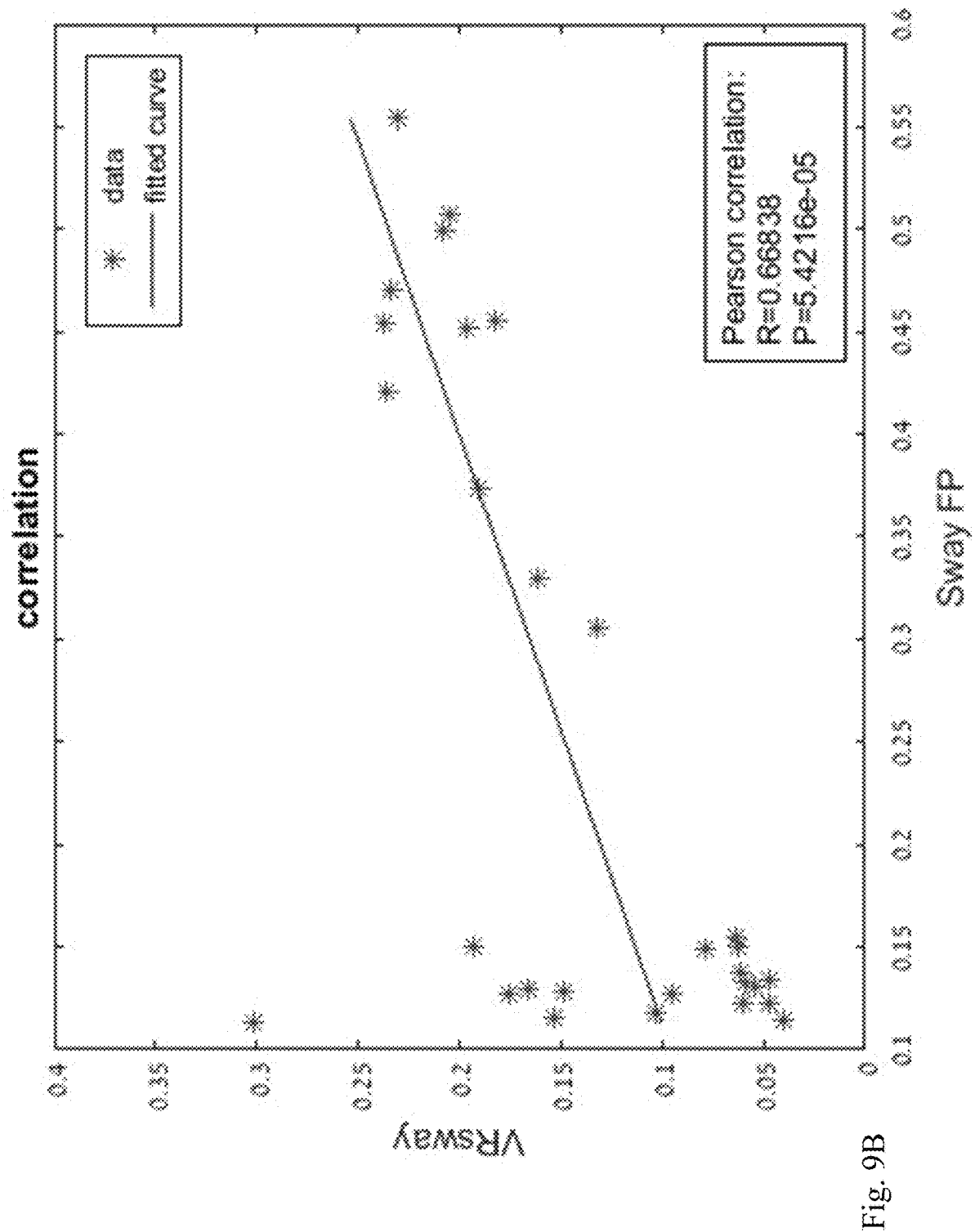
Figure 9C:
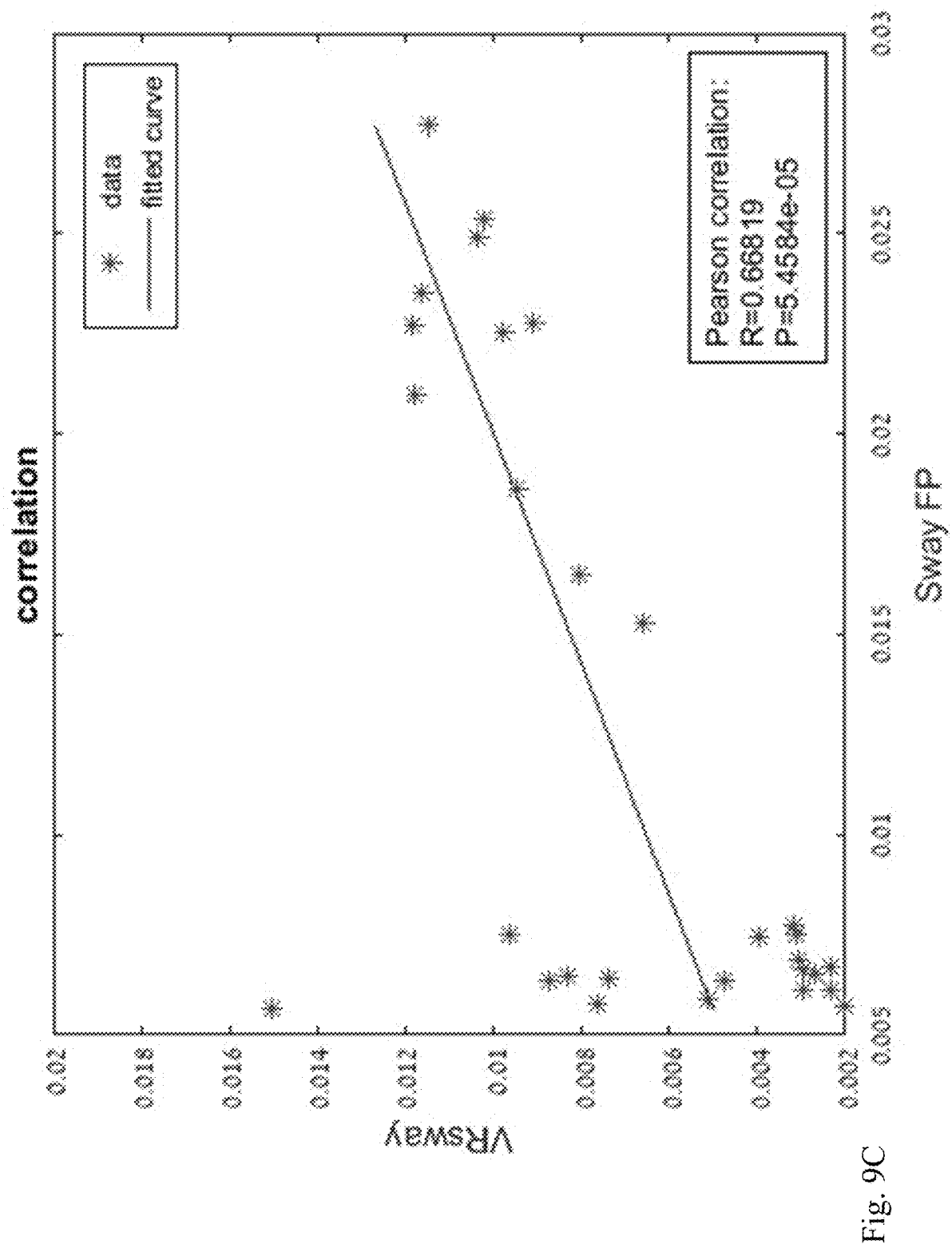
Figure 9D:
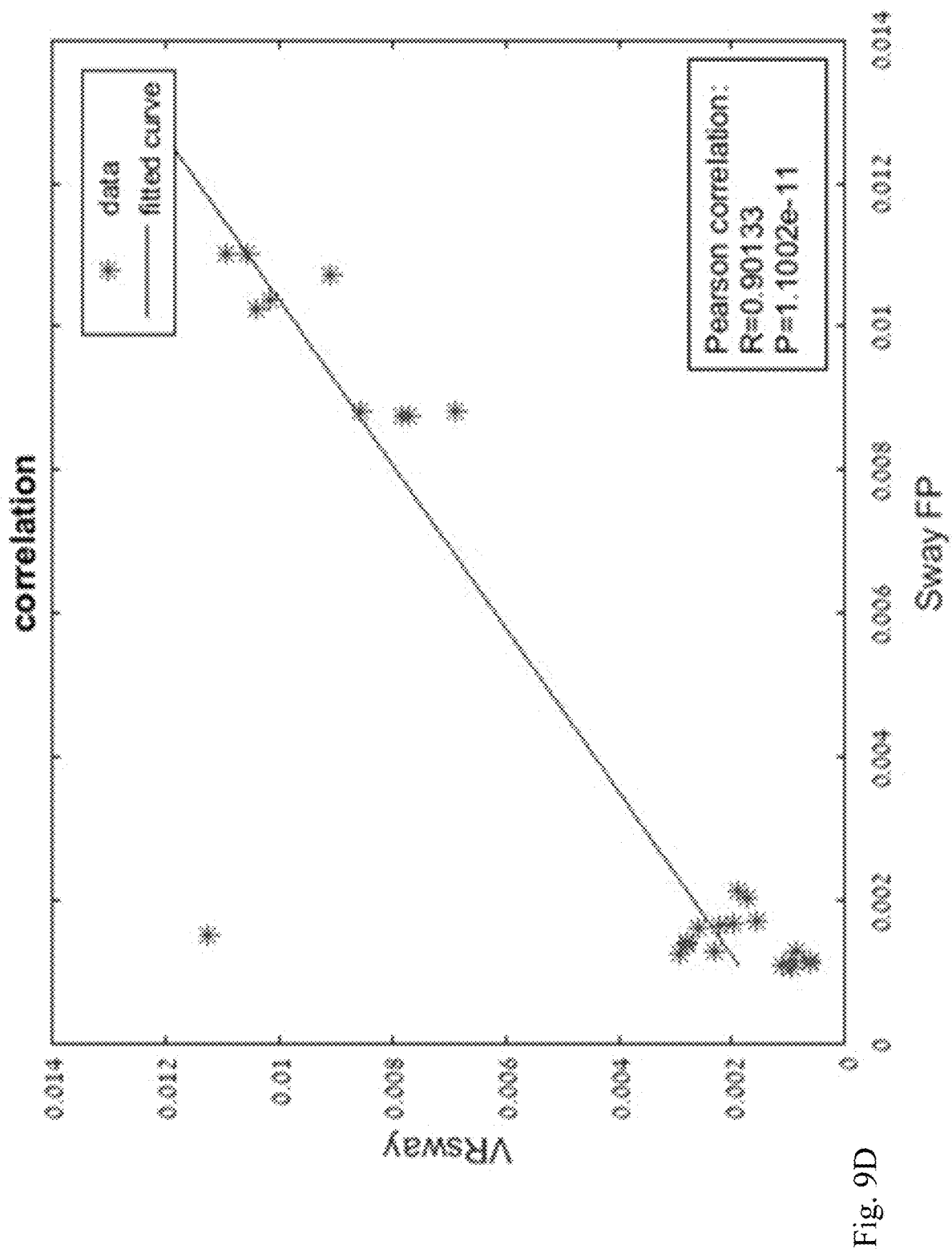
Figure 9E:
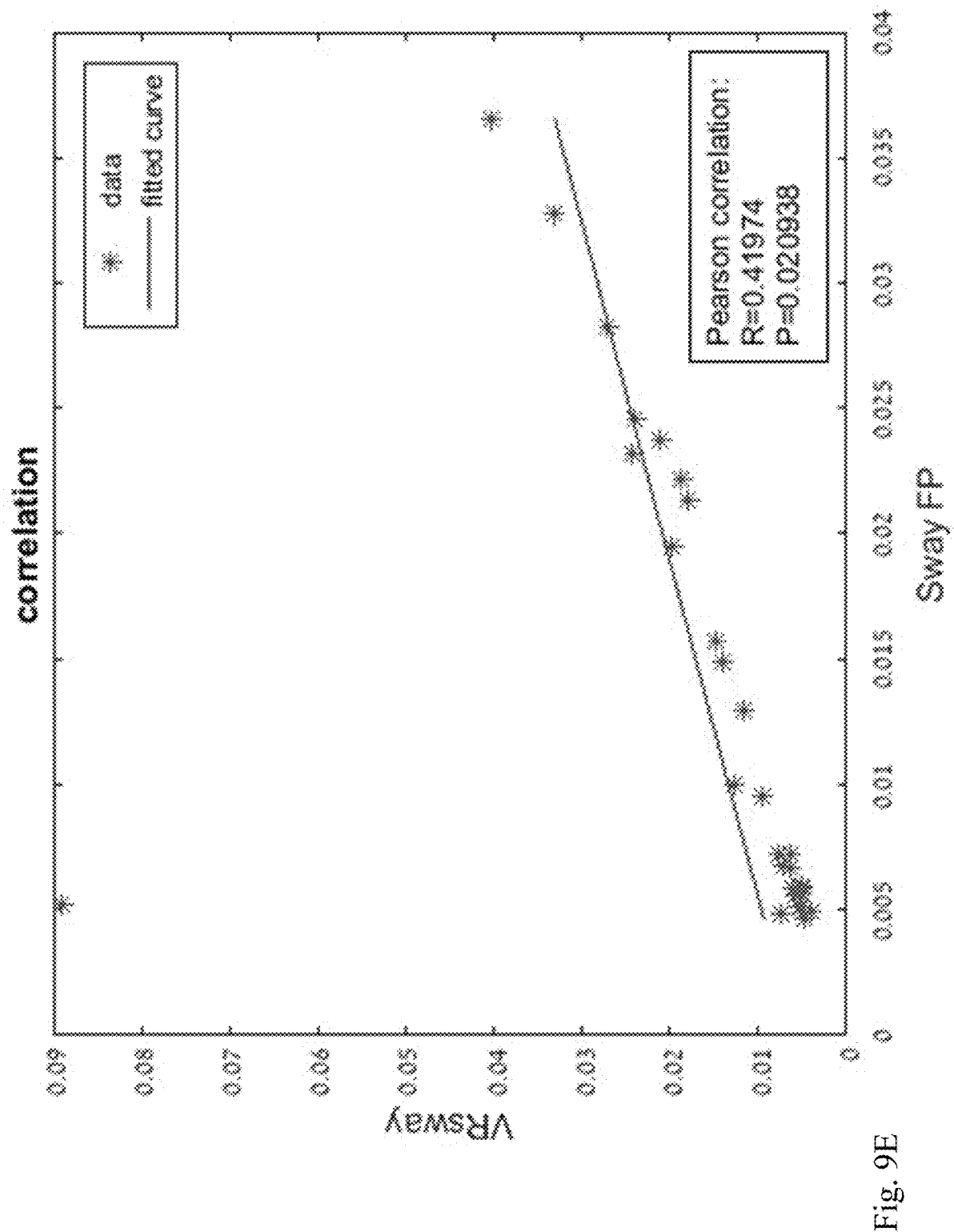
Figure 9F:
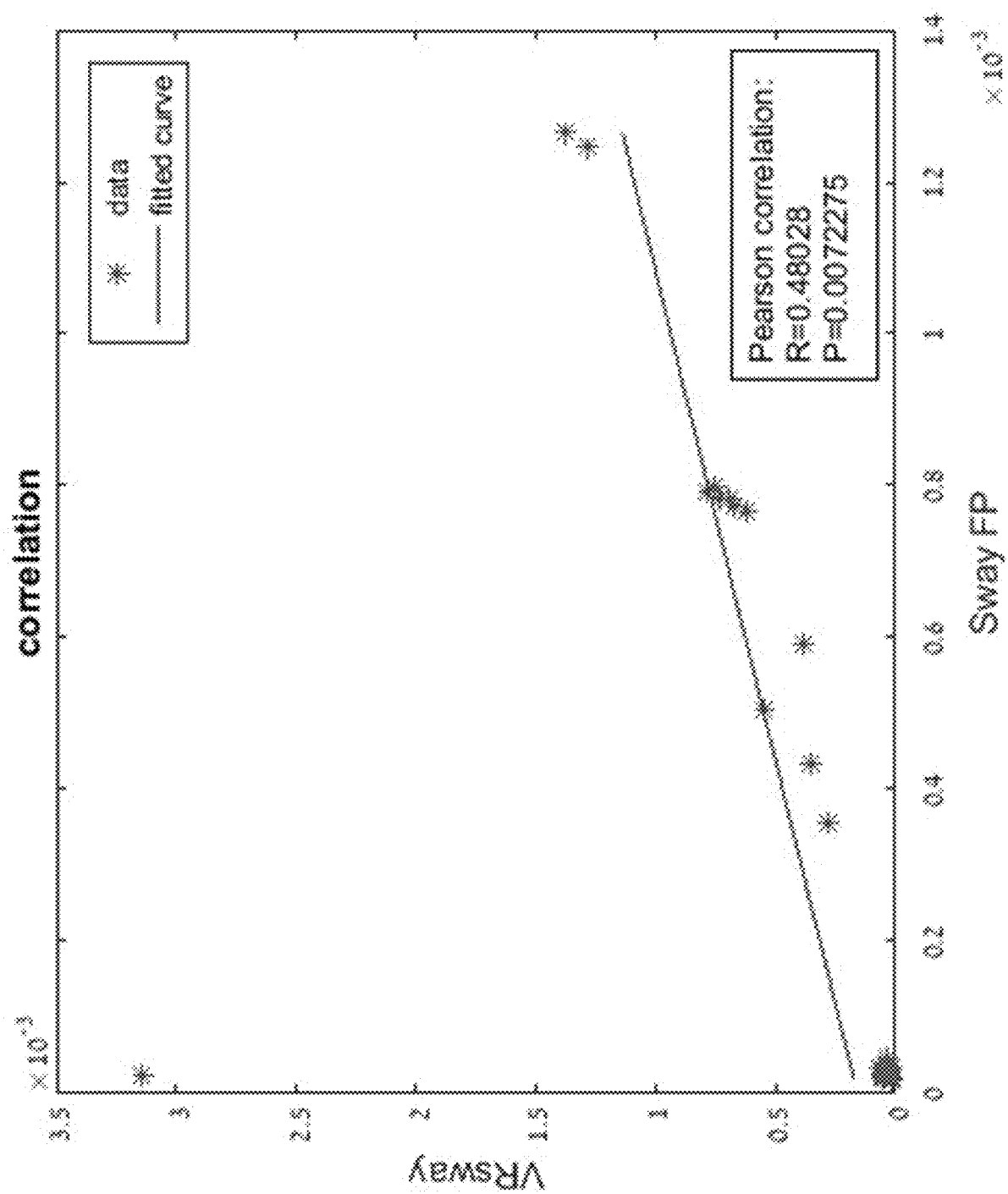
Figure 10A:
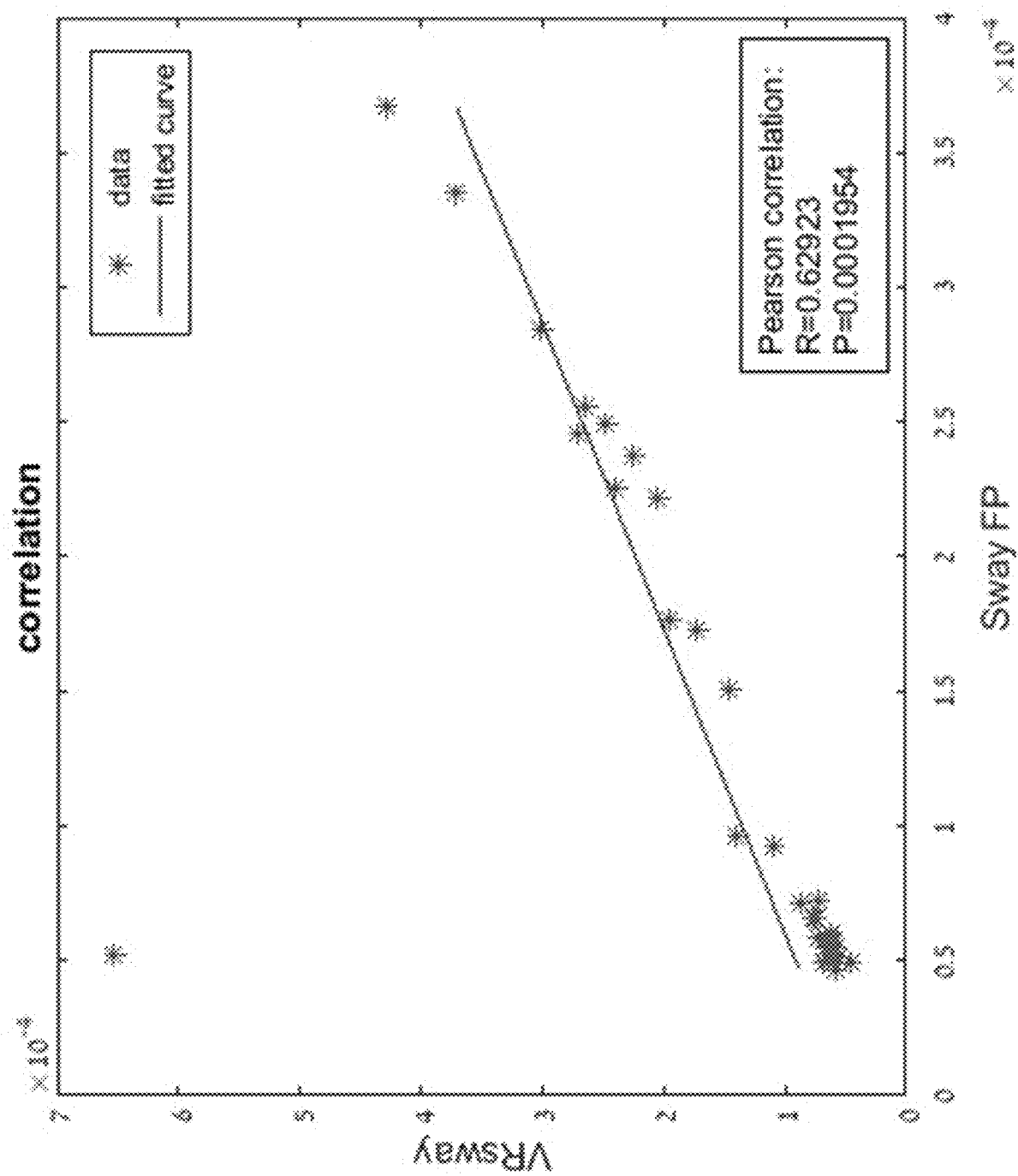
FIGS. 10A-10F show graphs of Pearson correlations of VR and force plate methods for a first patient according to an embodiment of the present disclosure.
Figure 10B:
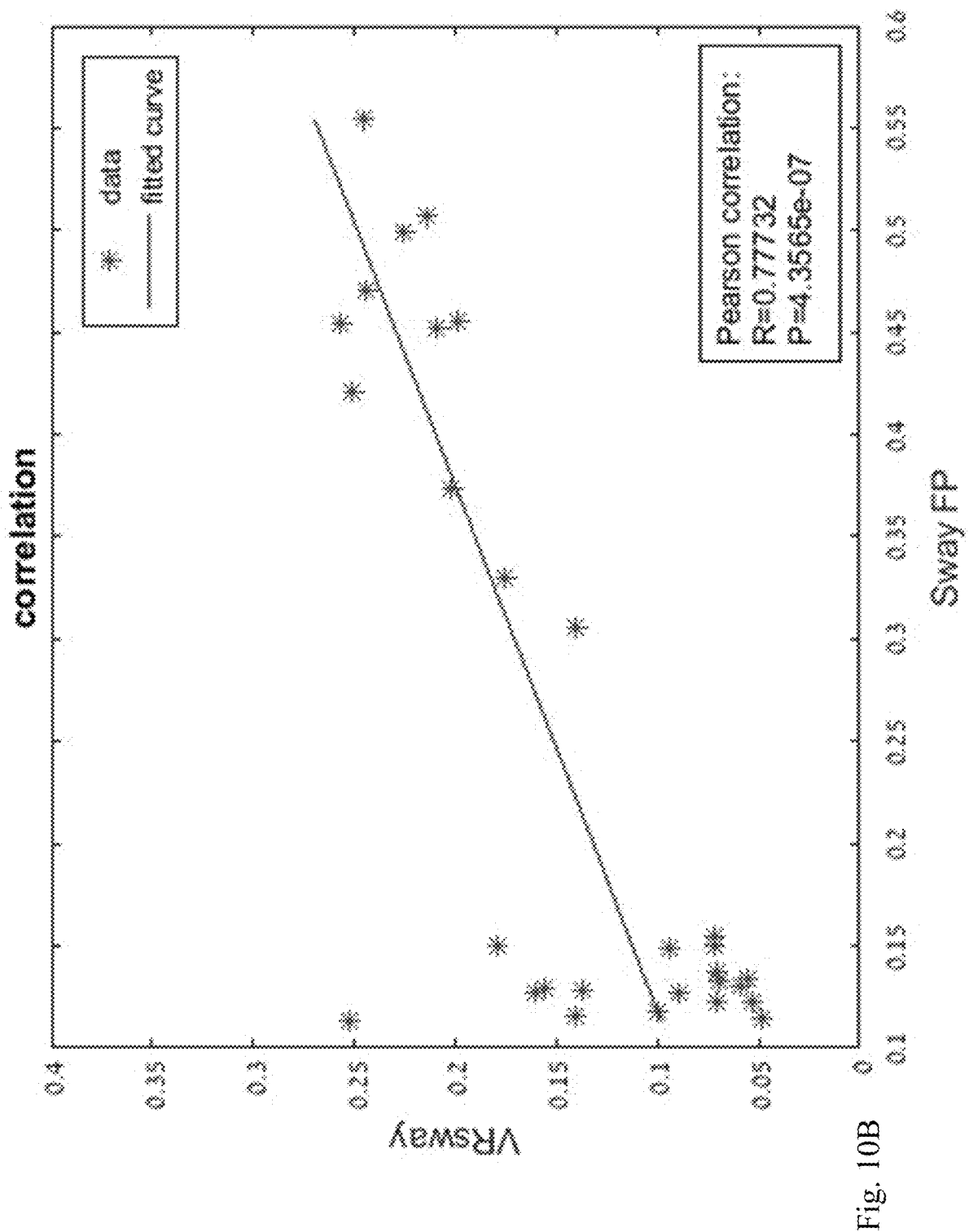
Figure 10C:
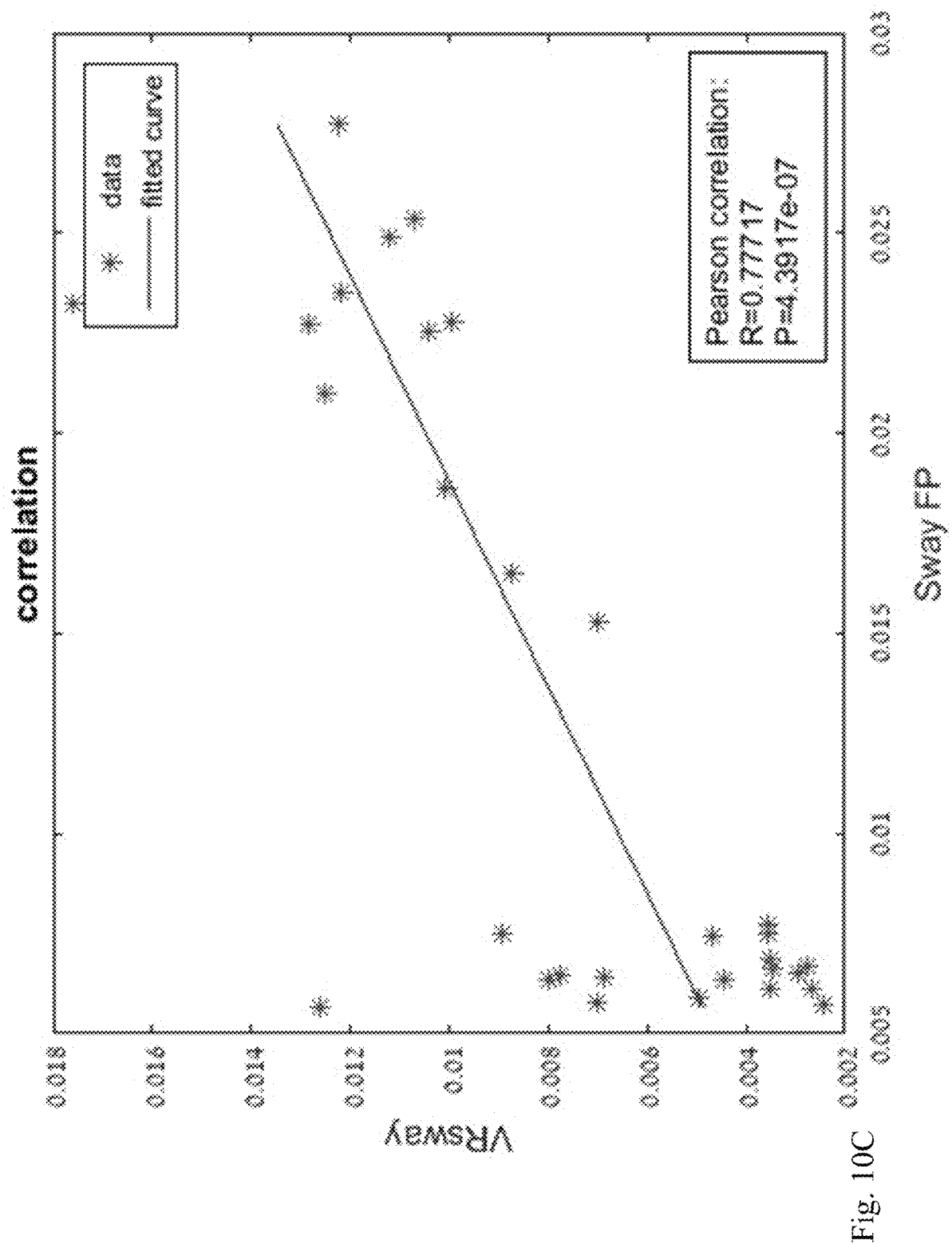
Figure 10D:
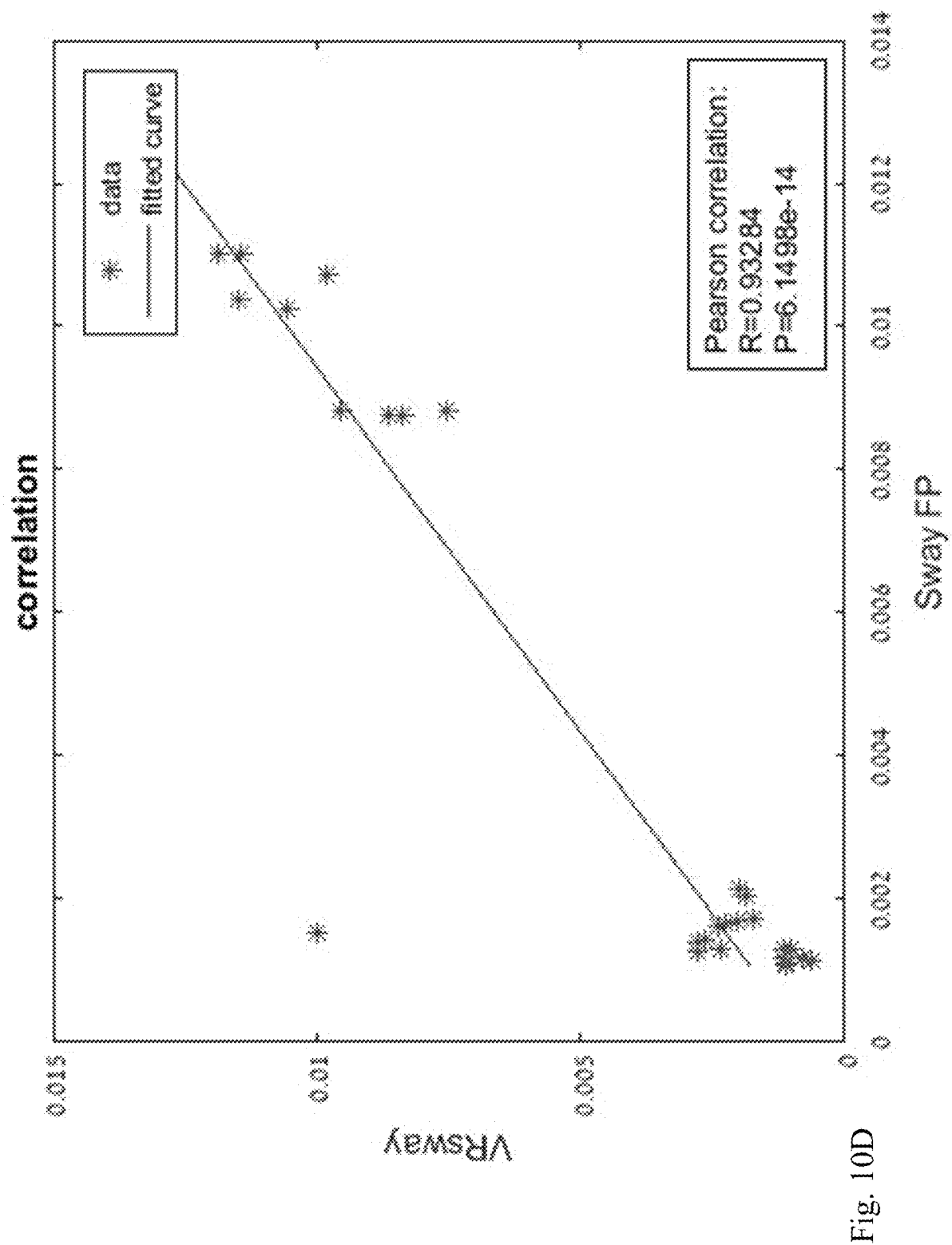
Figure 10E:
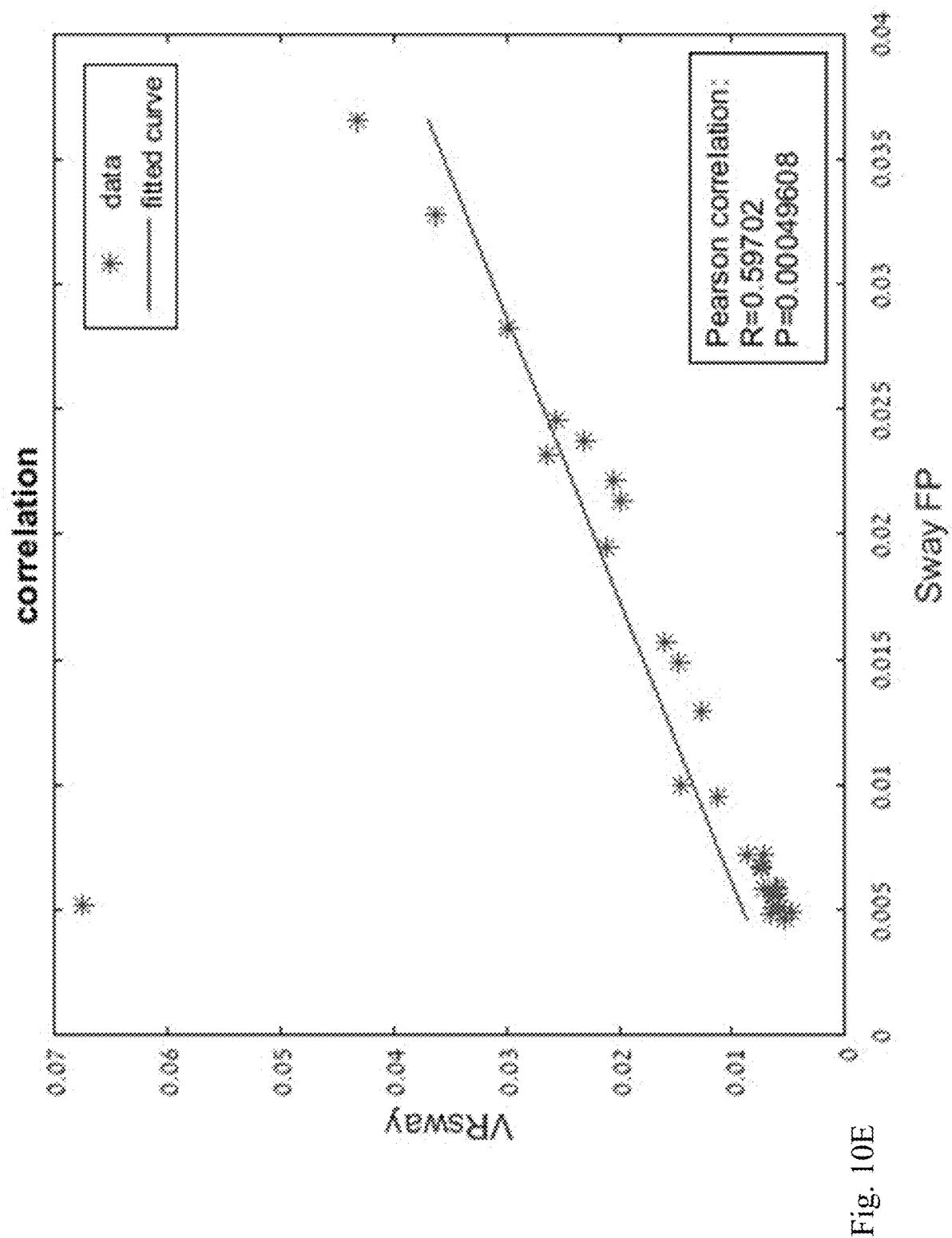
Figure 10F:
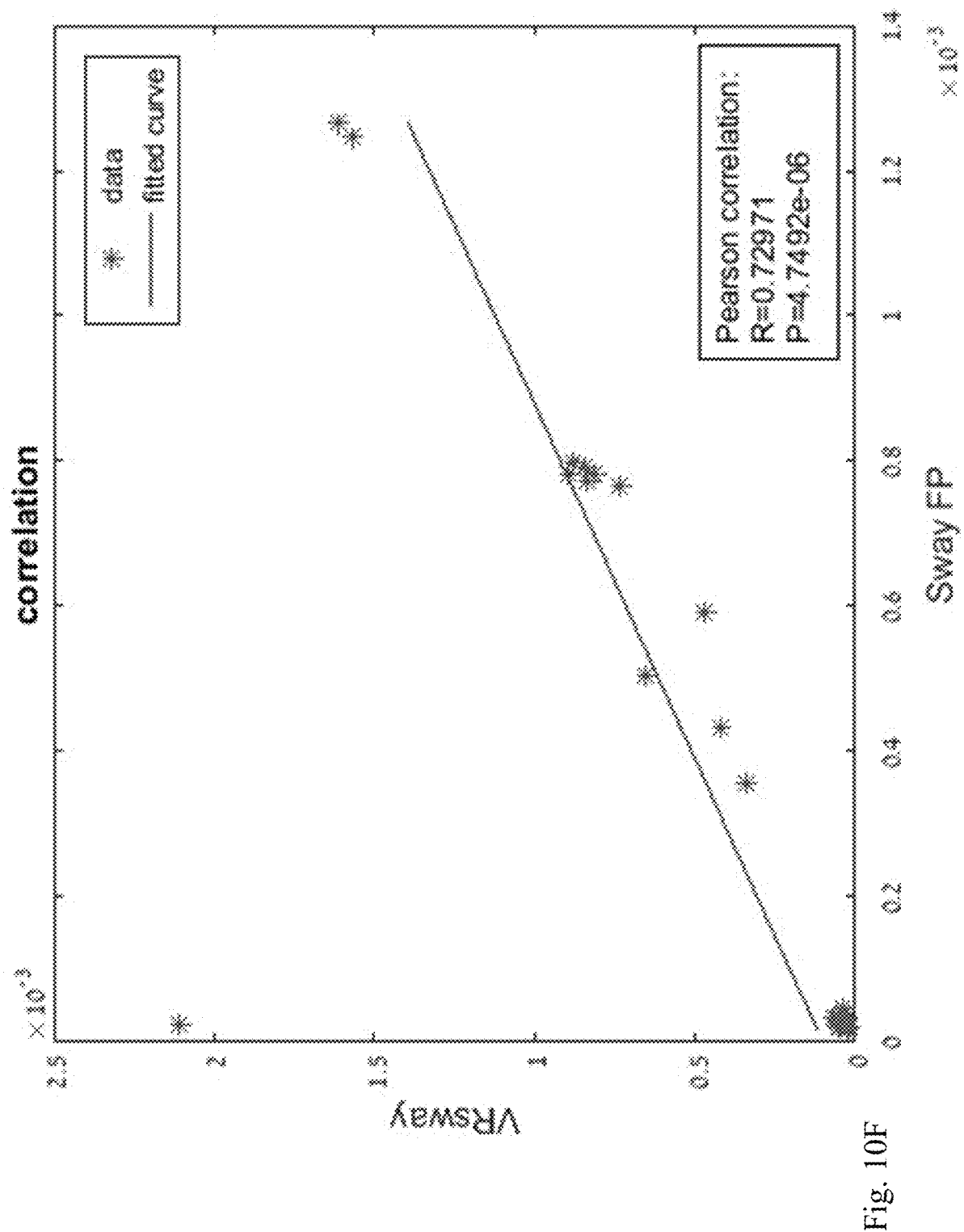
Figure 11A:
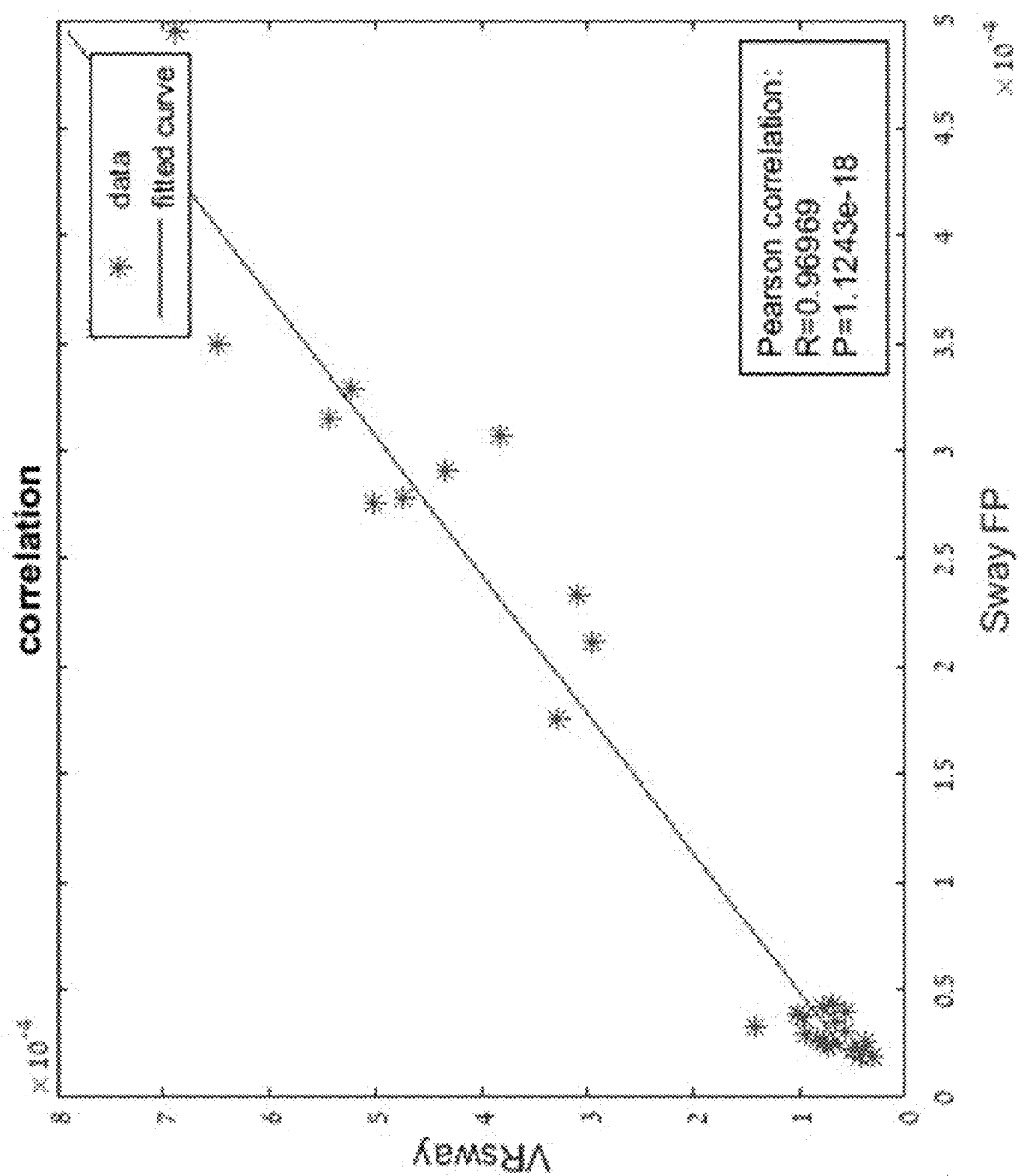
FIGS. 11A-11F show graphs of Pearson correlations of VR and force plate methods for a second patient according to an embodiment of the present disclosure.
Figure 11B:
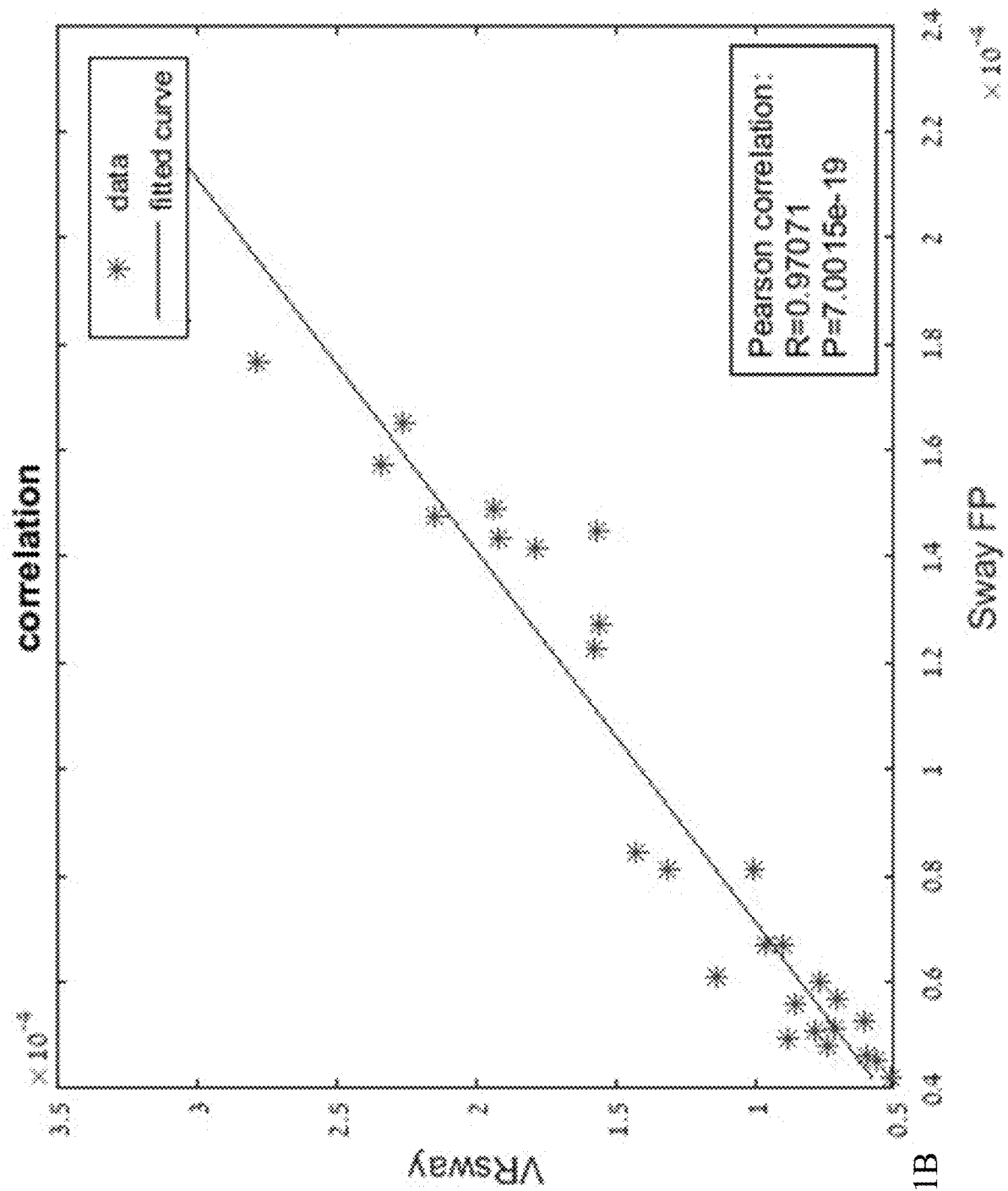
Figure 11C:
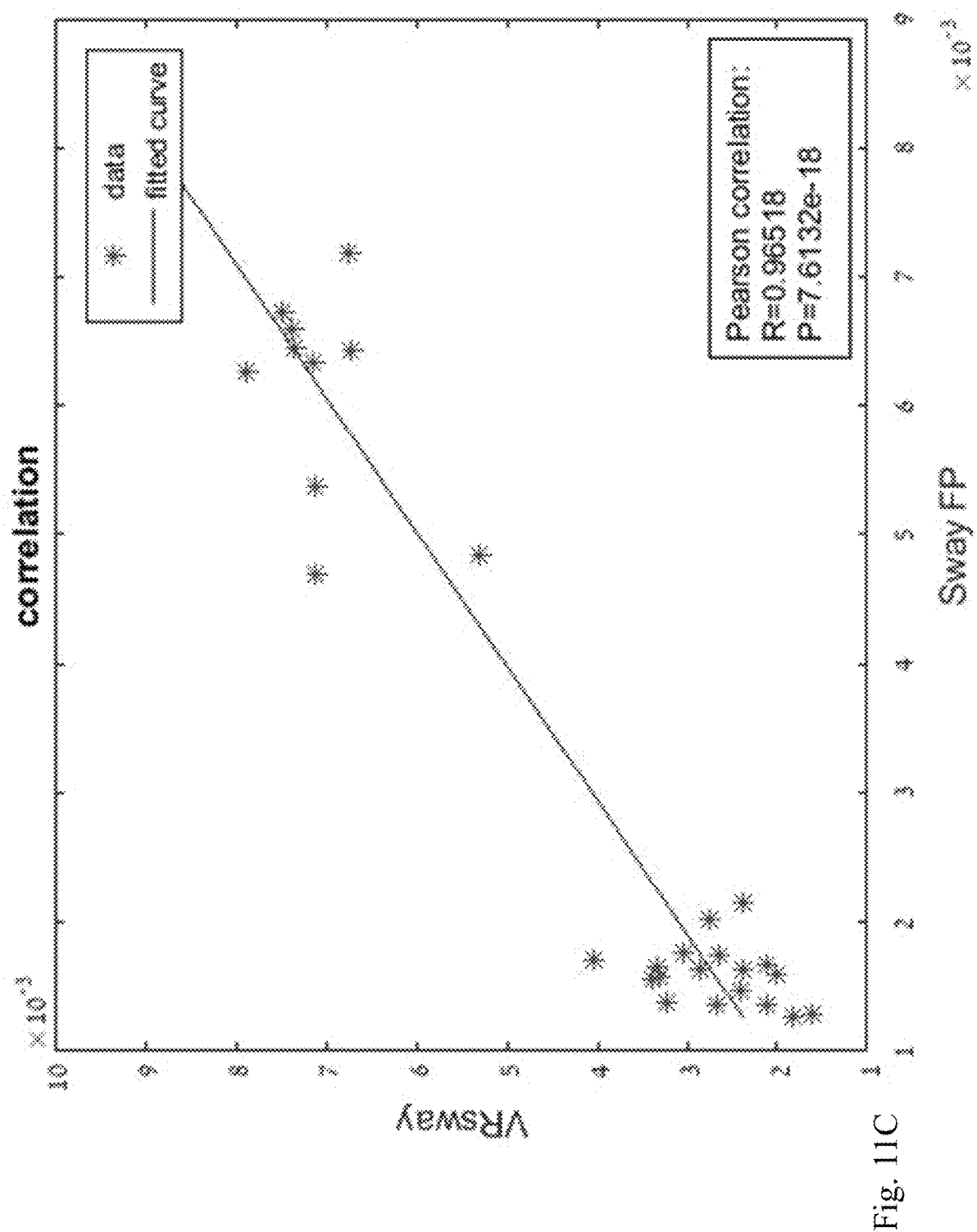
Figure 11D:
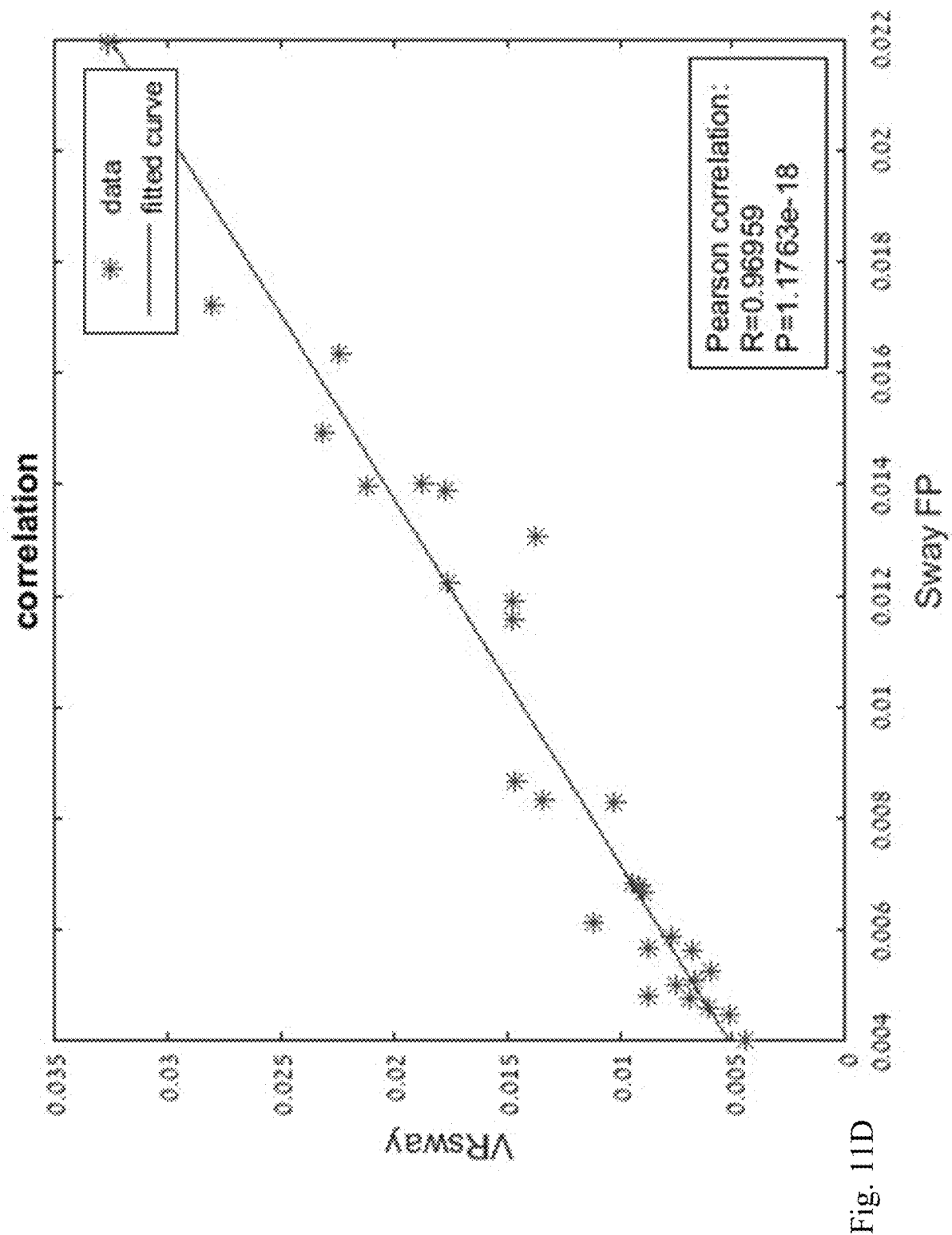
Figure 11E:
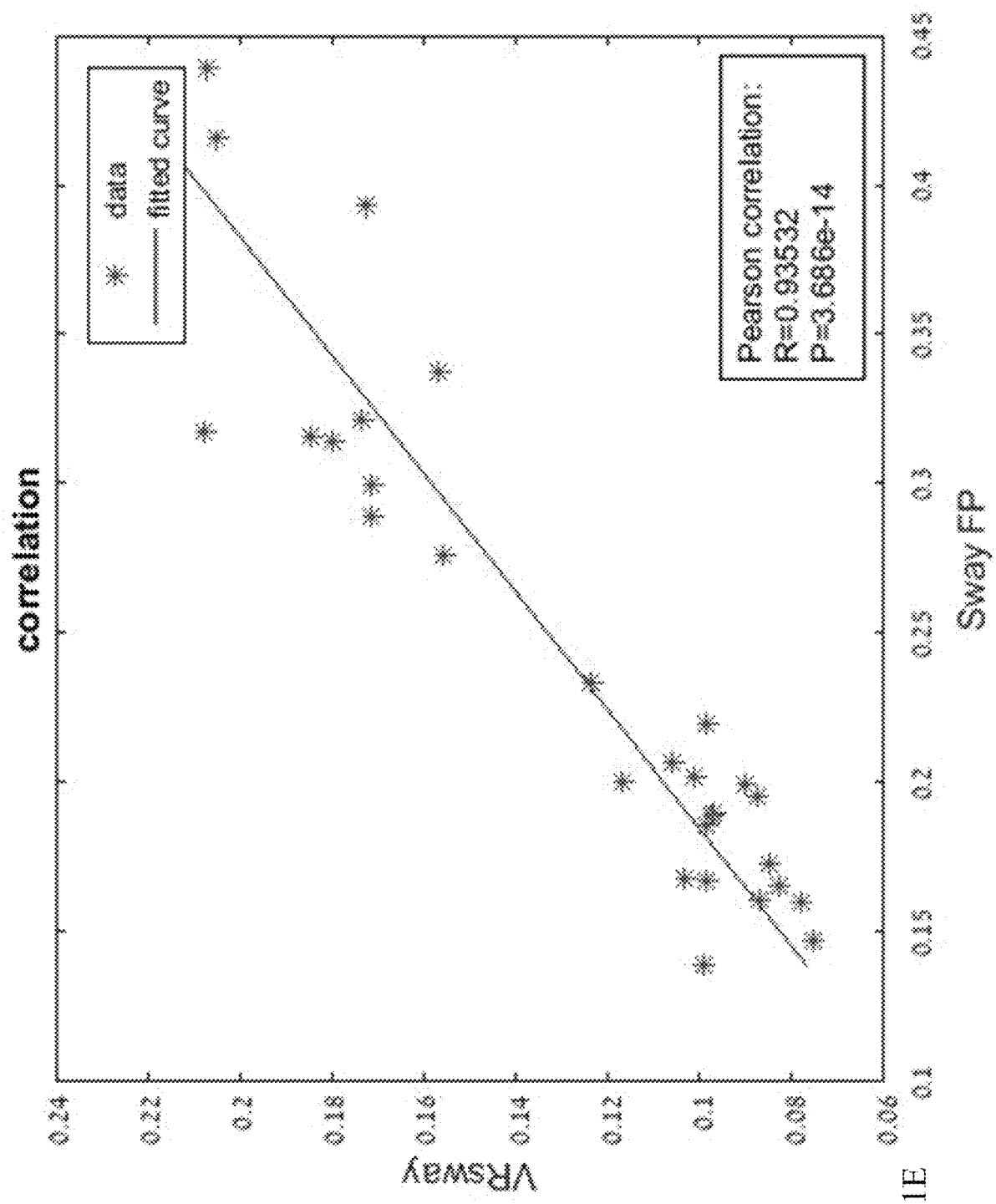
Figure 11F:
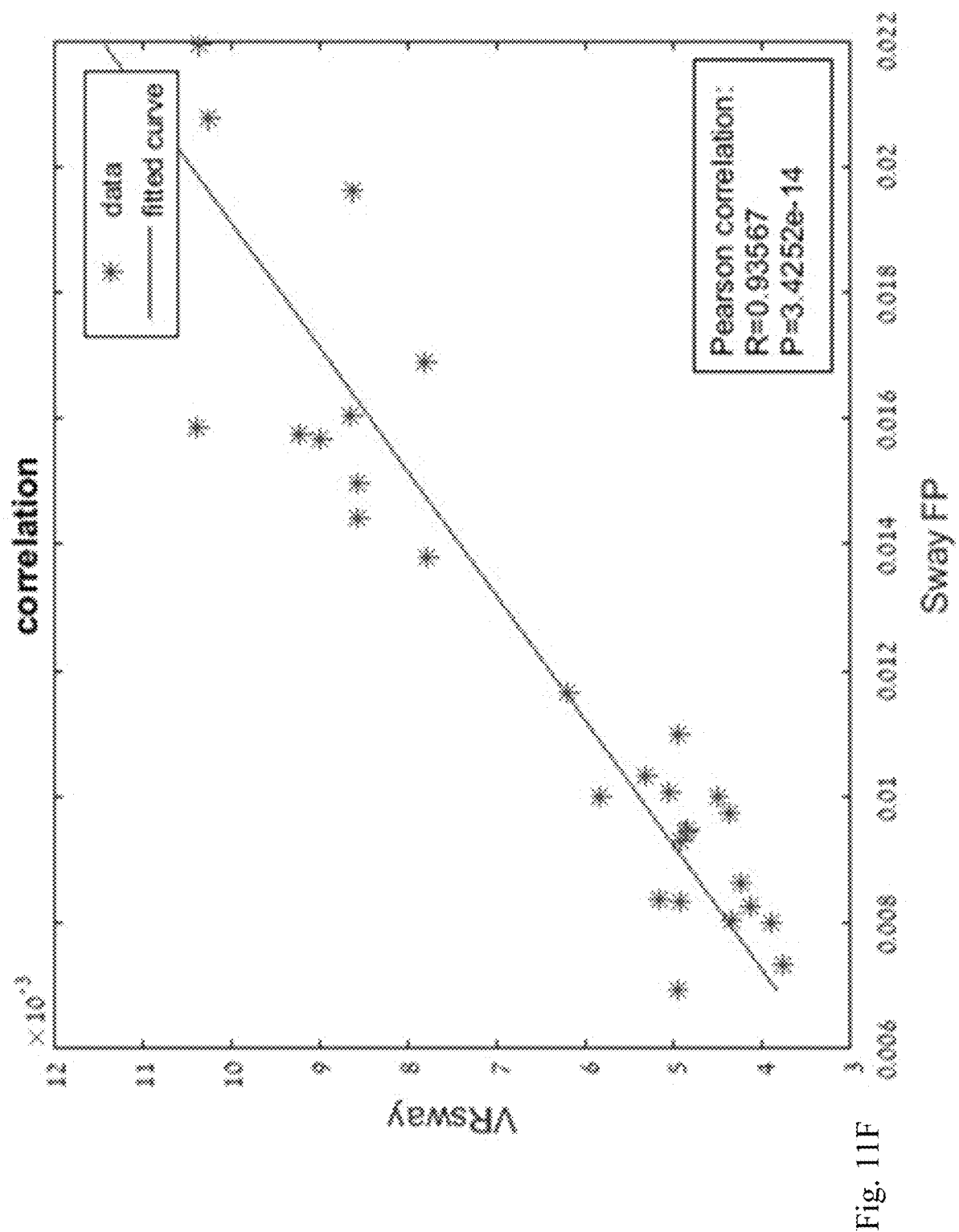
Figure 12A:
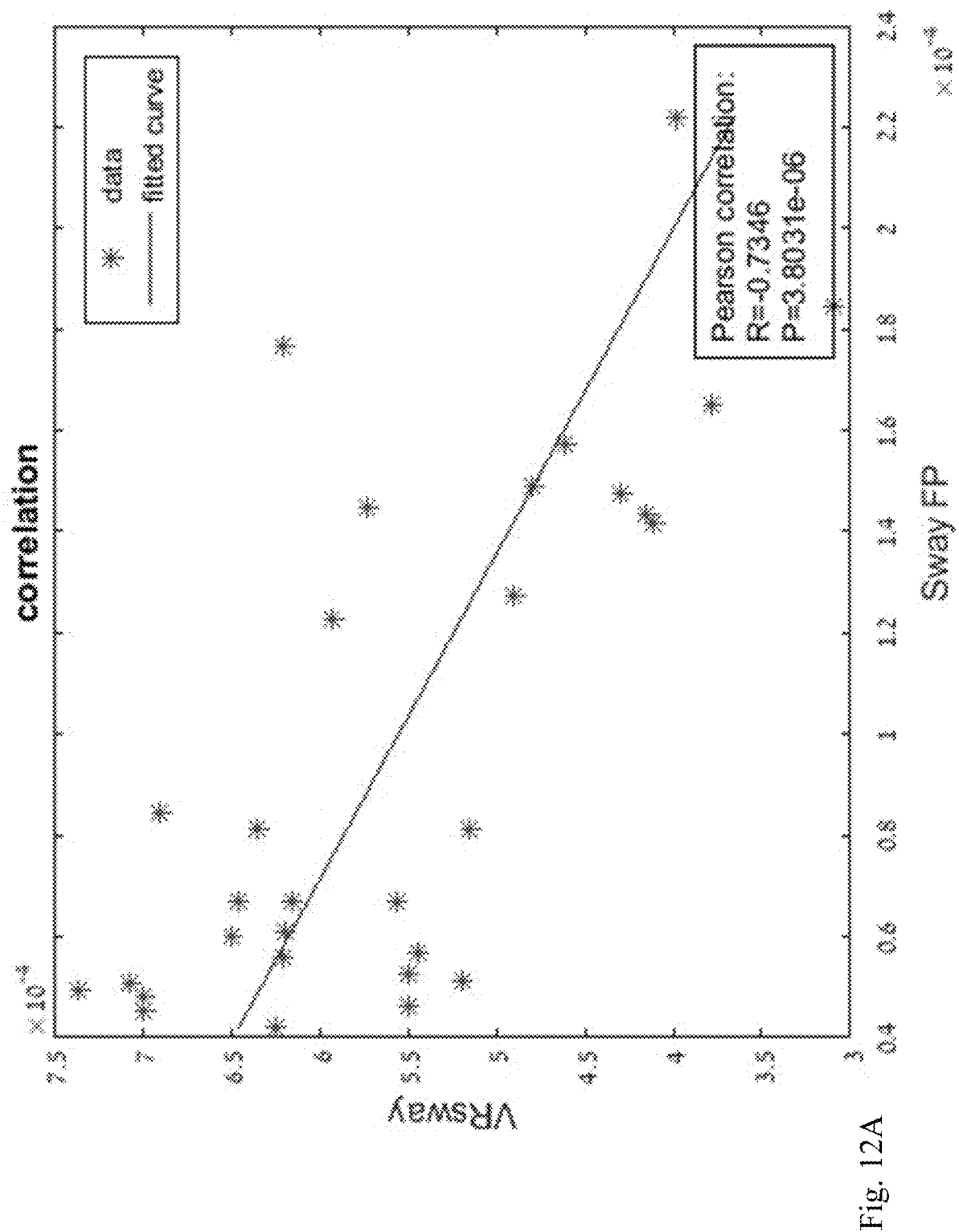
FIGS. 12A-12F shows graphs of Pearson correlations of VR and force plate methods for a second patient according to an embodiment of the present disclosure.
Figure 12B:
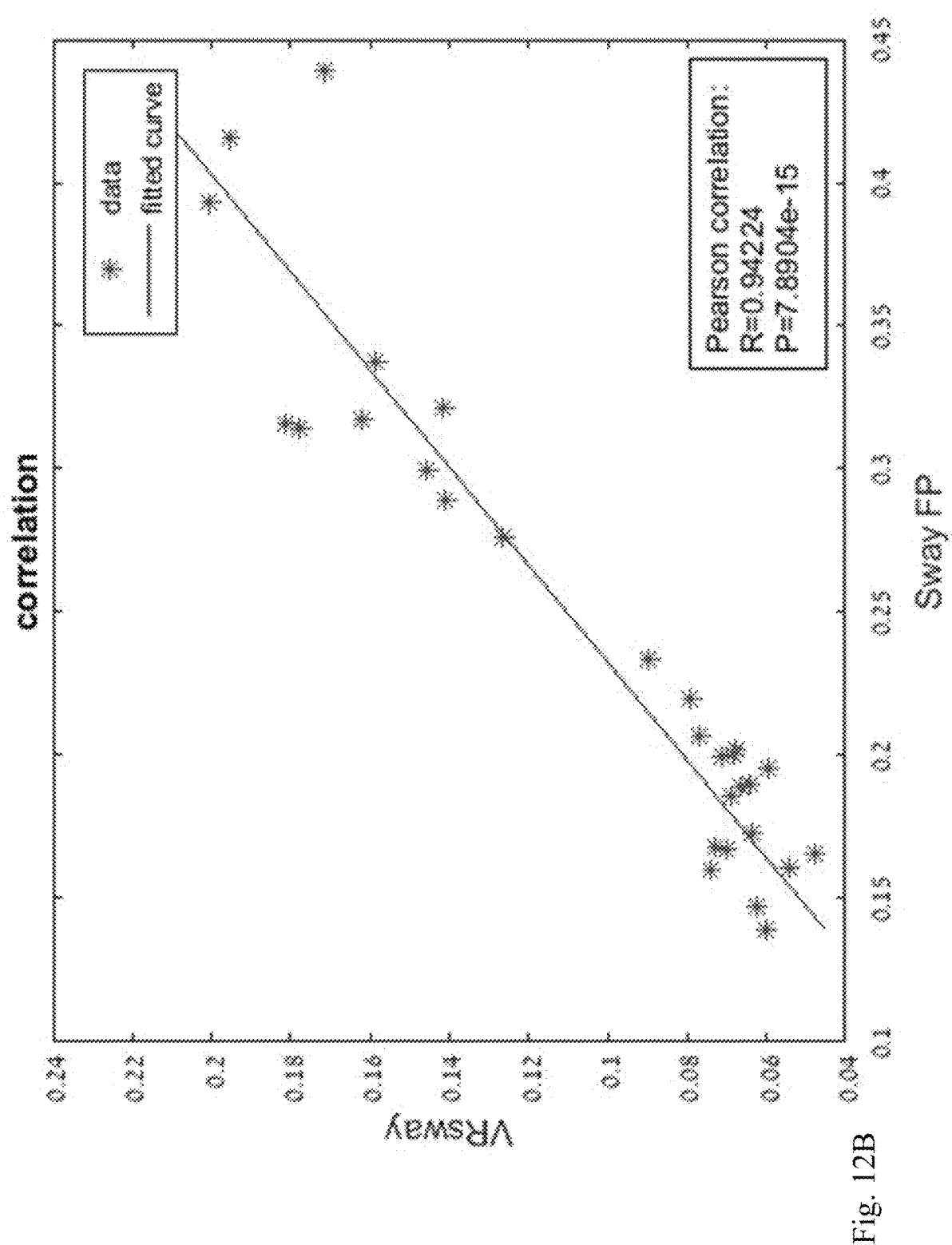
Figure 12C:
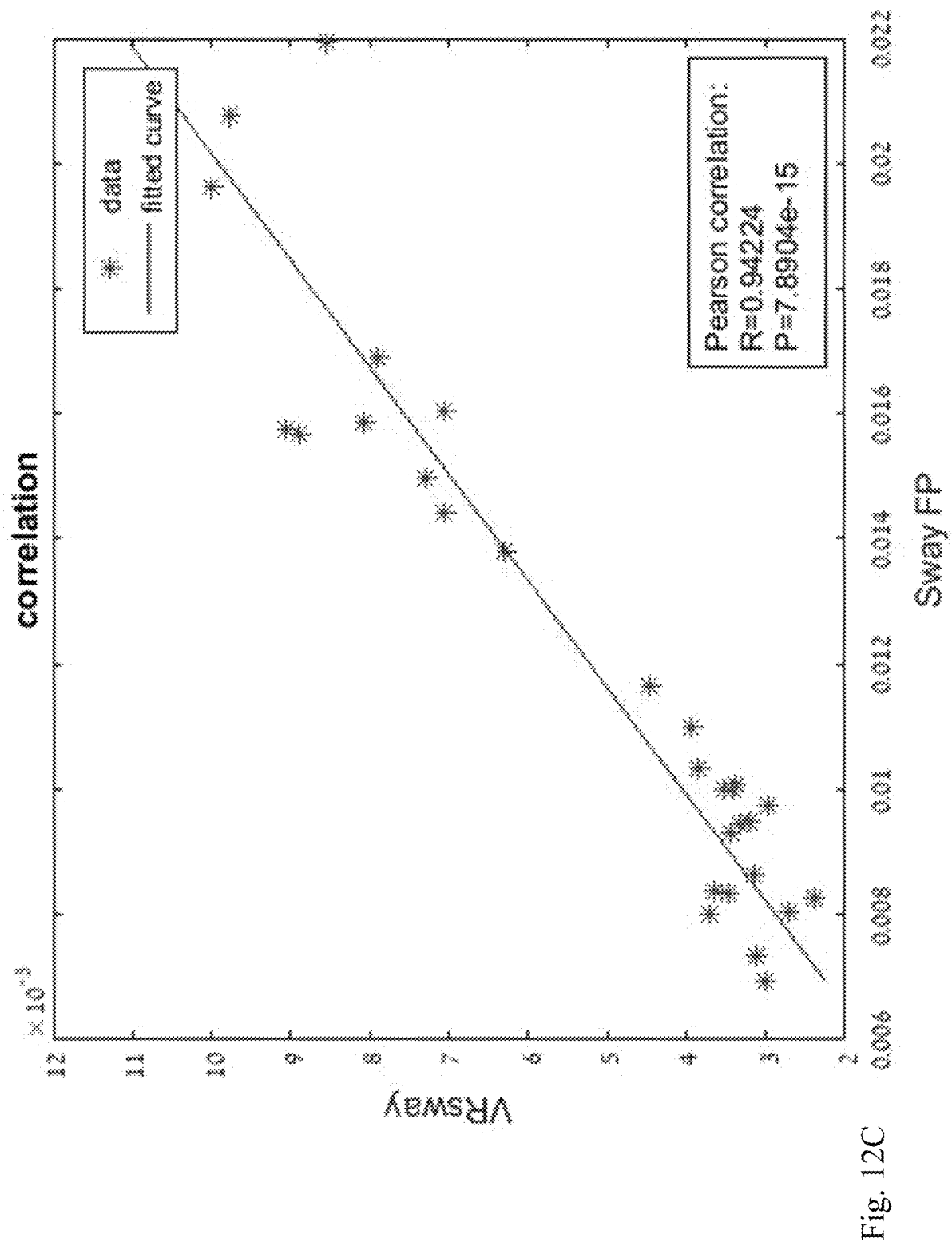
Figure 12D:
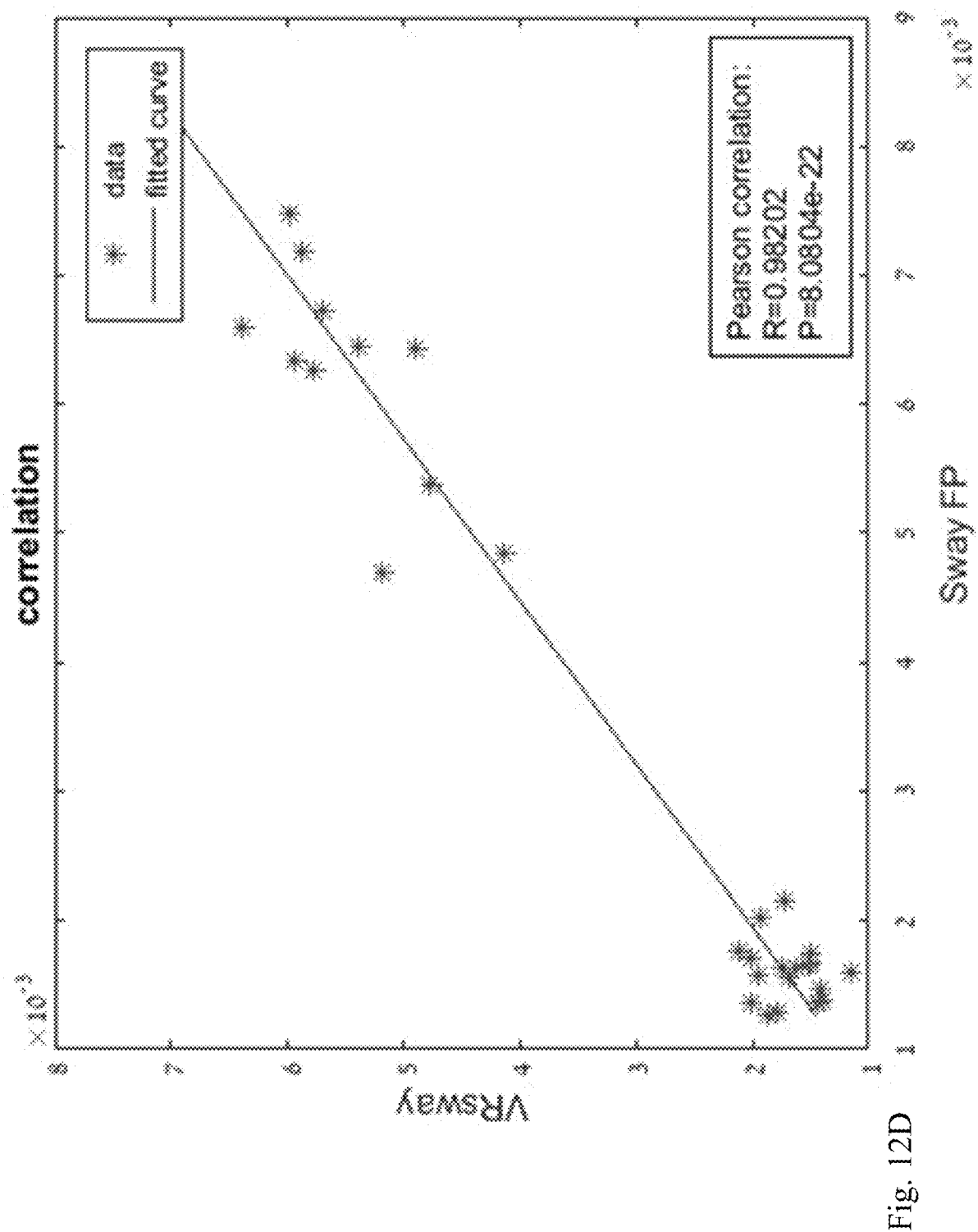
Figure 12E:
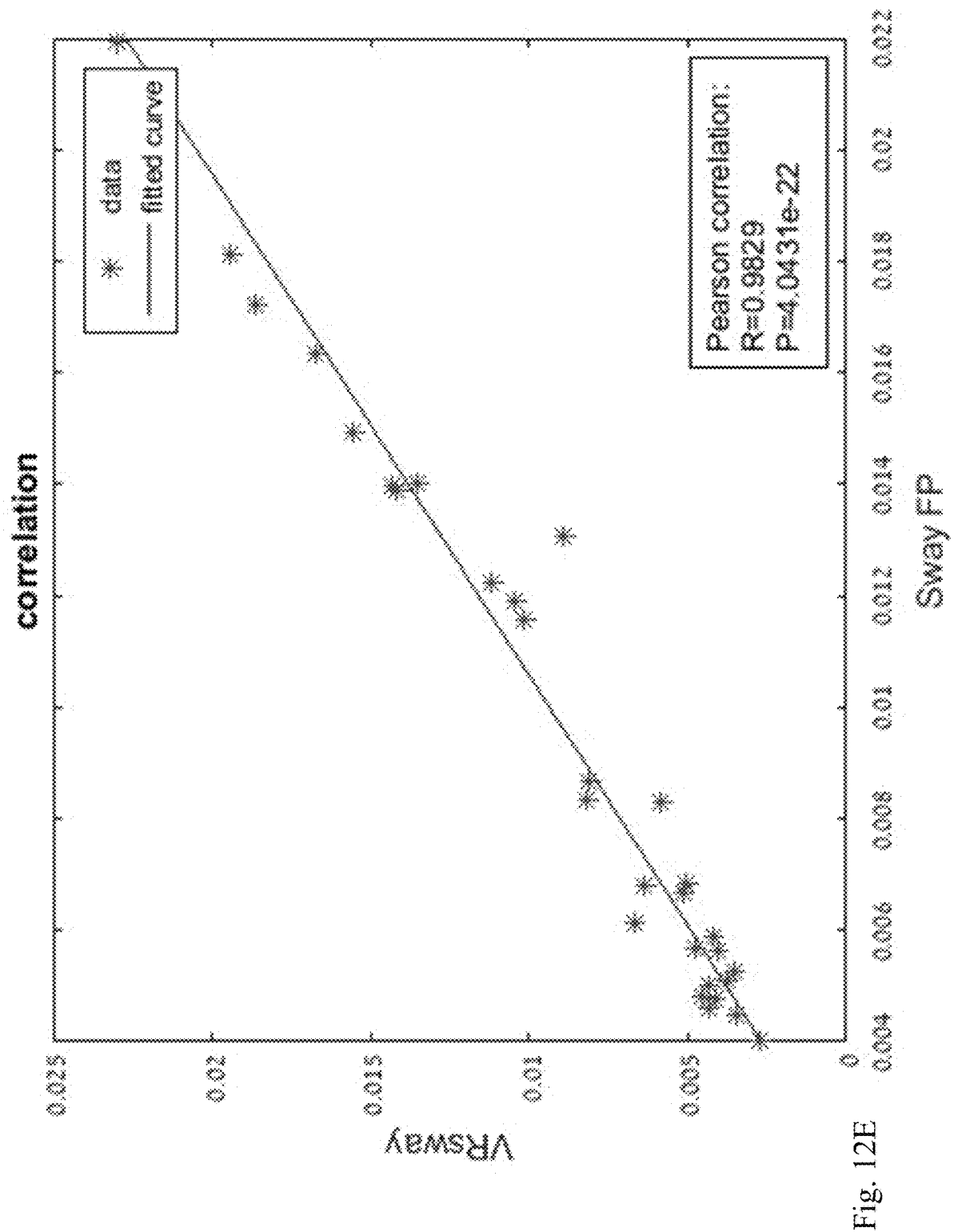
Figure 12F:
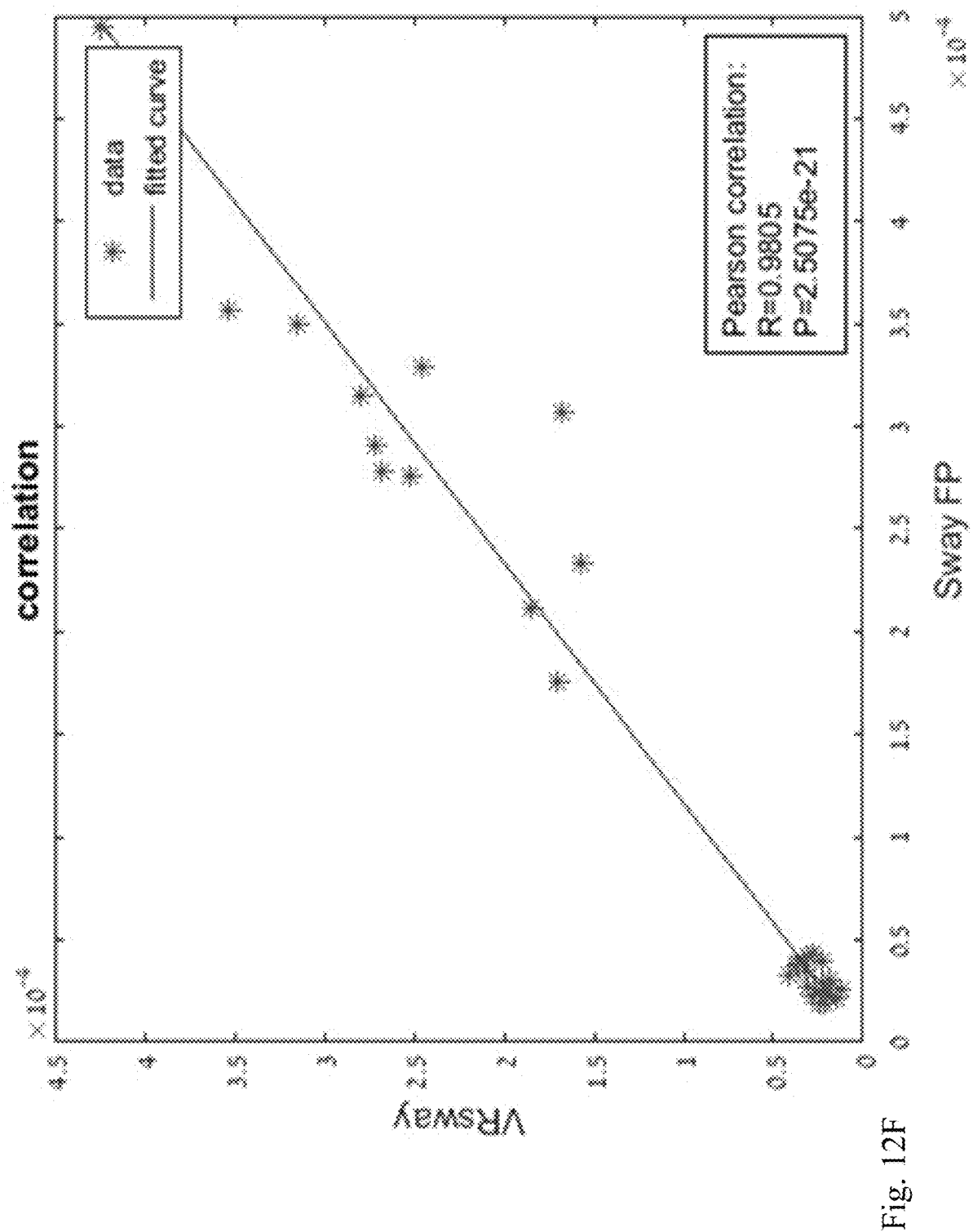
Figure 13A:
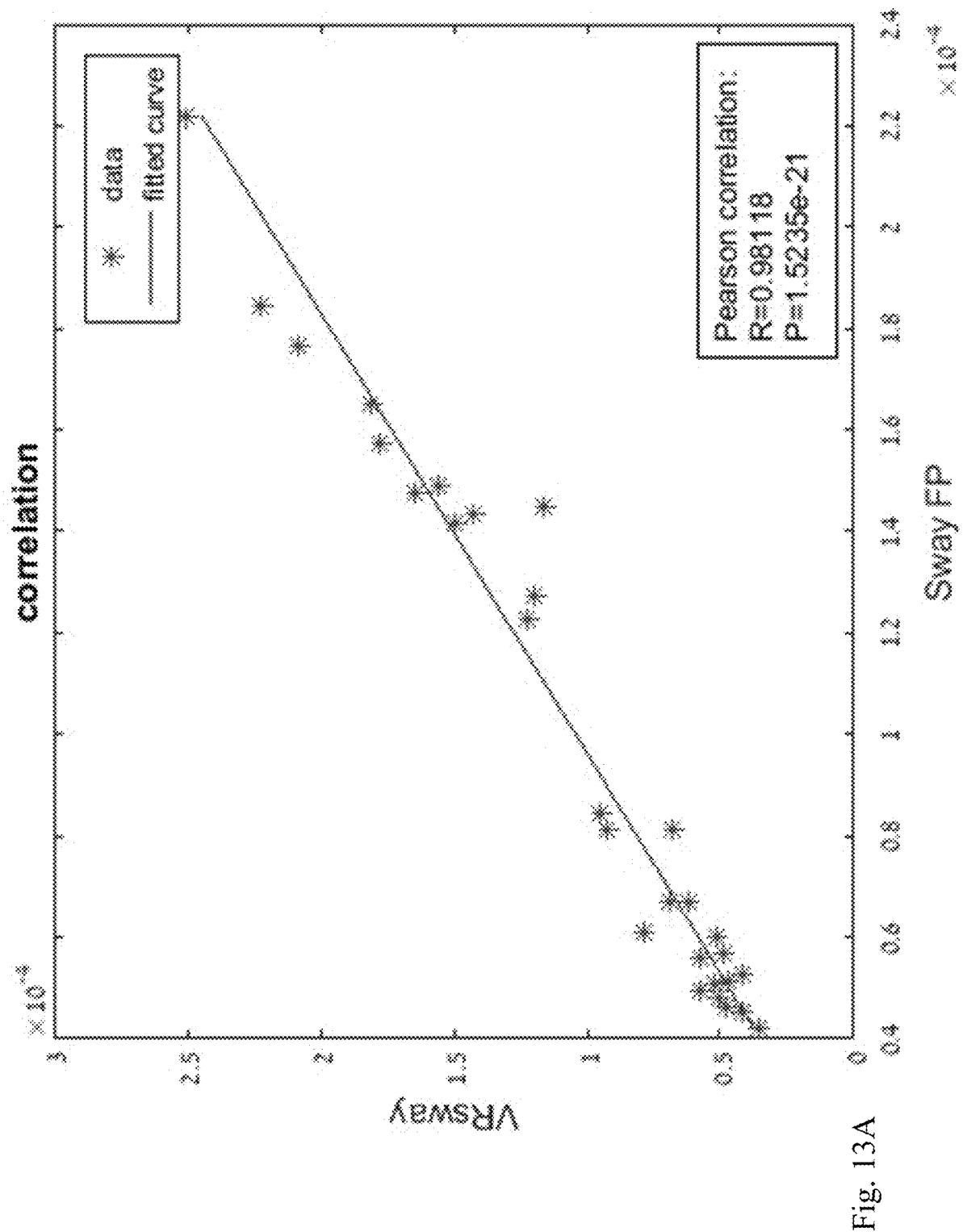
FIGS. 13A-13F shows graphs of Pearson correlations of VR and force plate methods for a second patient according to an embodiment of the present disclosure.
Figure 13B:
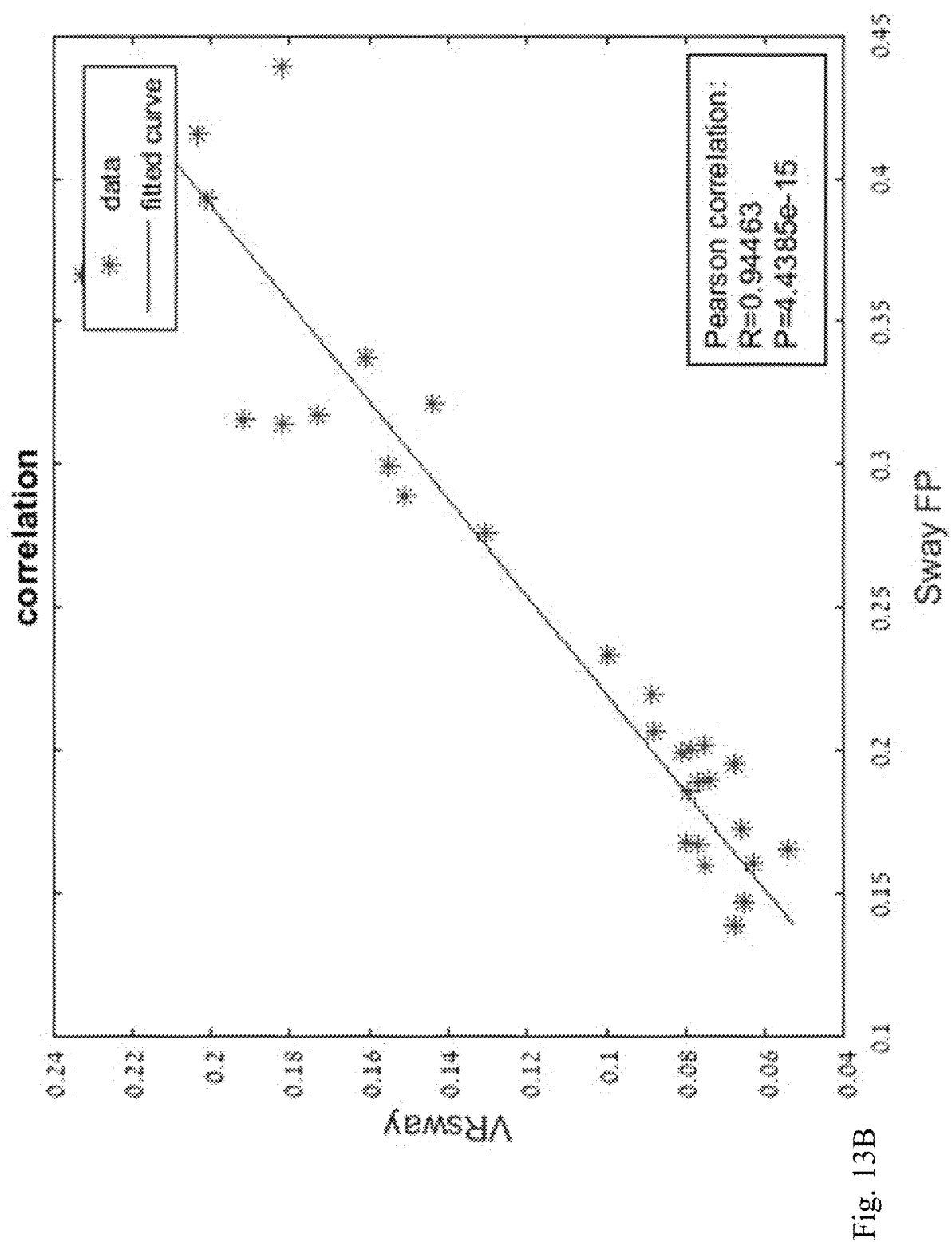
Figure 13C:
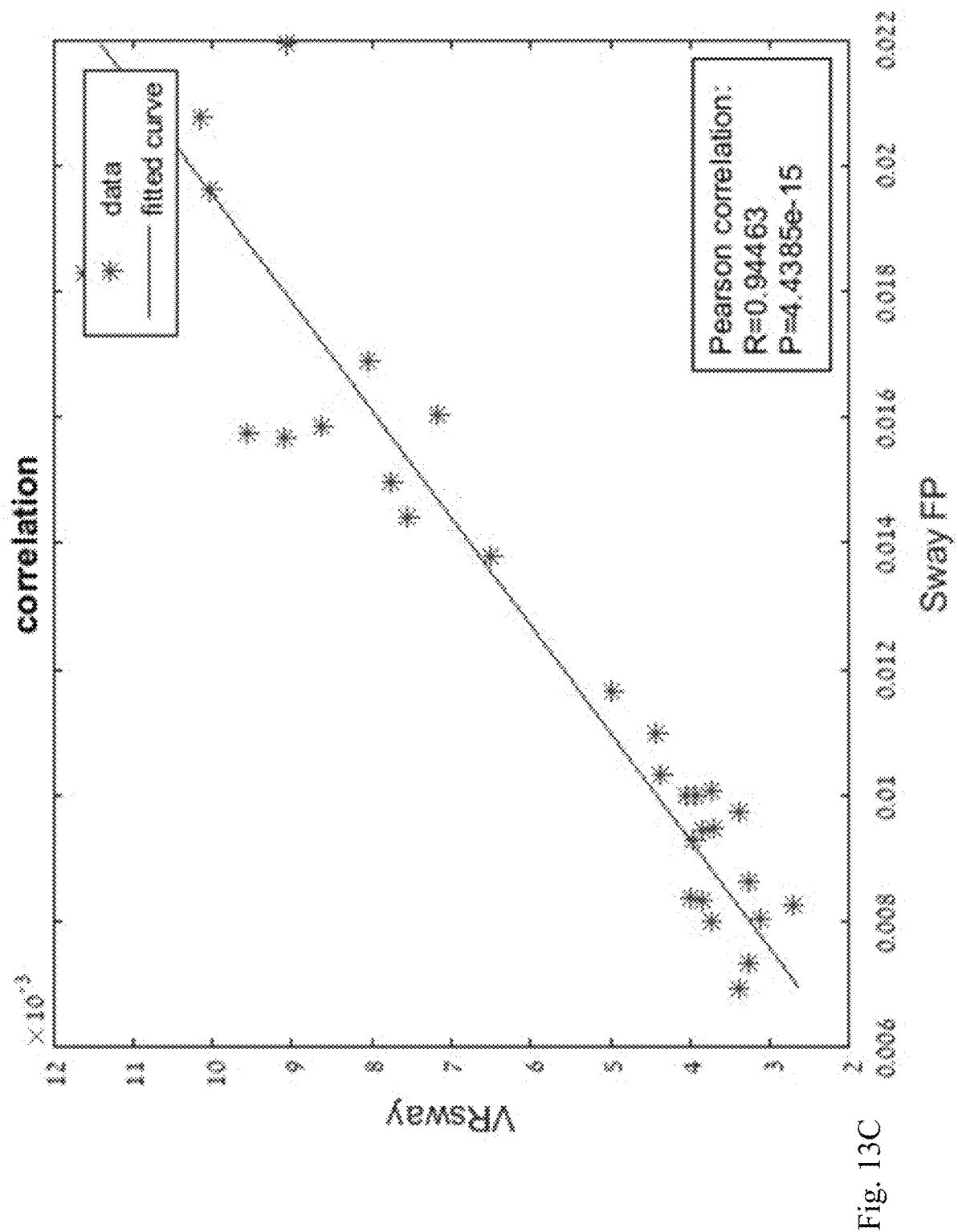
Figure 13D:
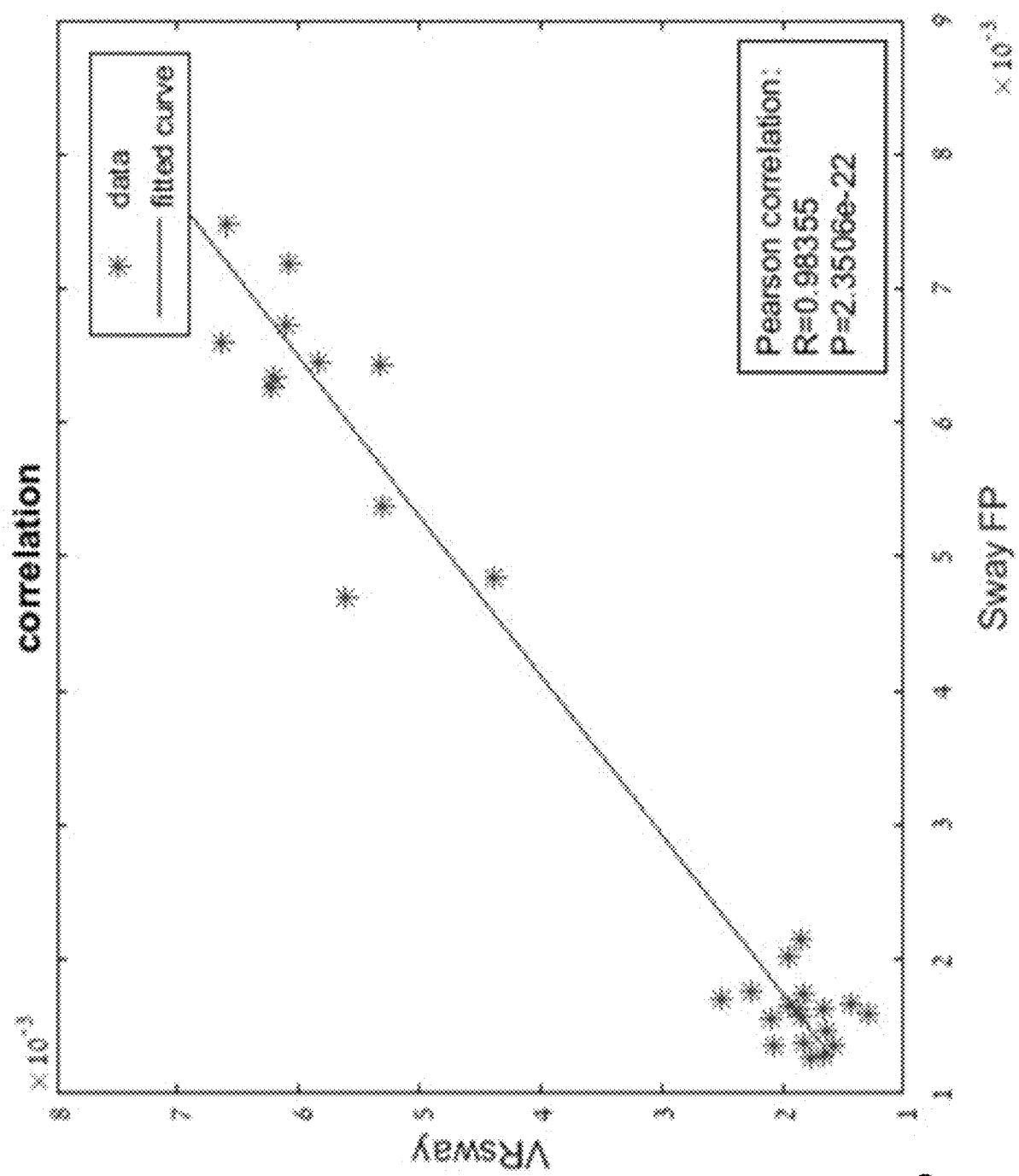
Figure 13E:
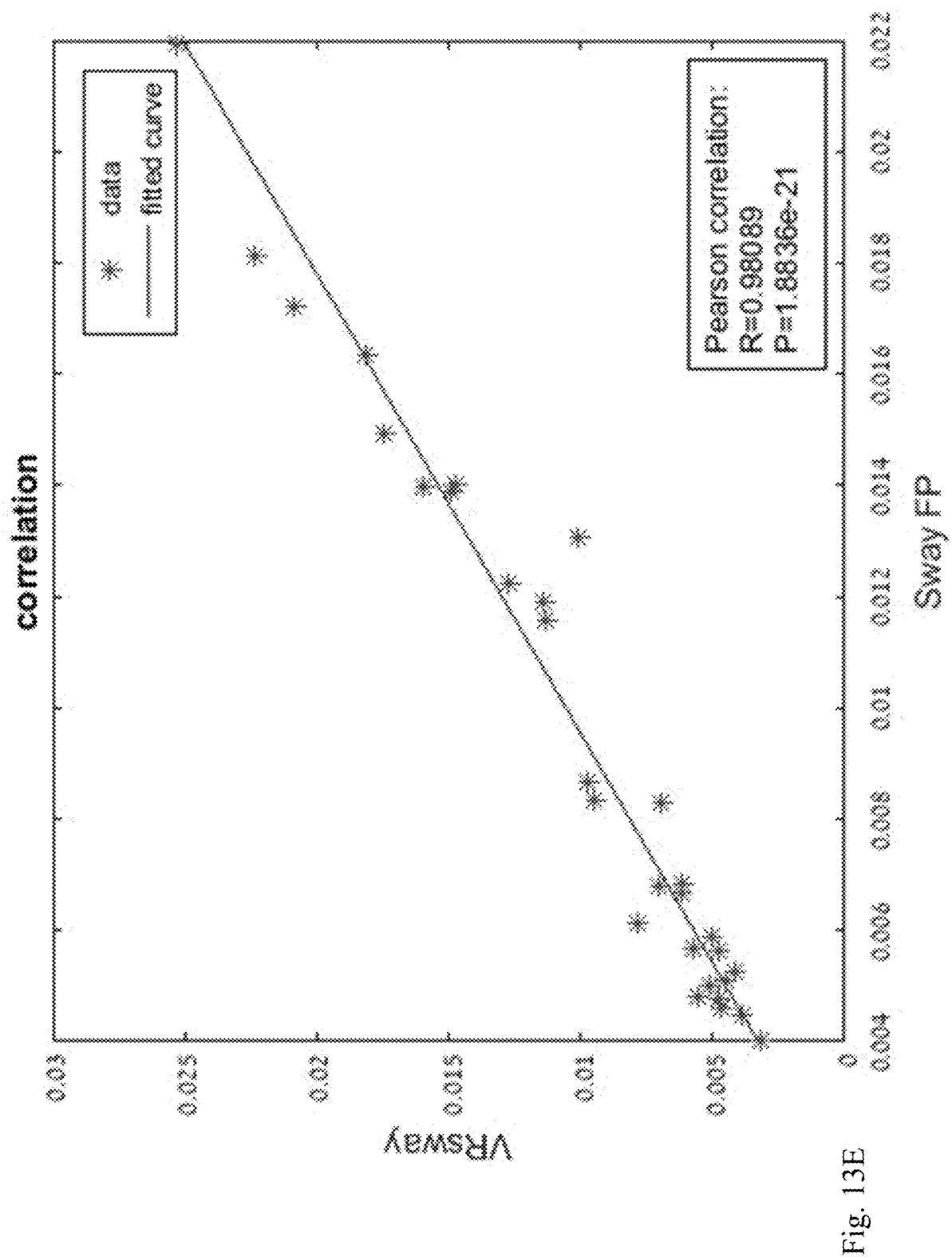
Figure 13F:
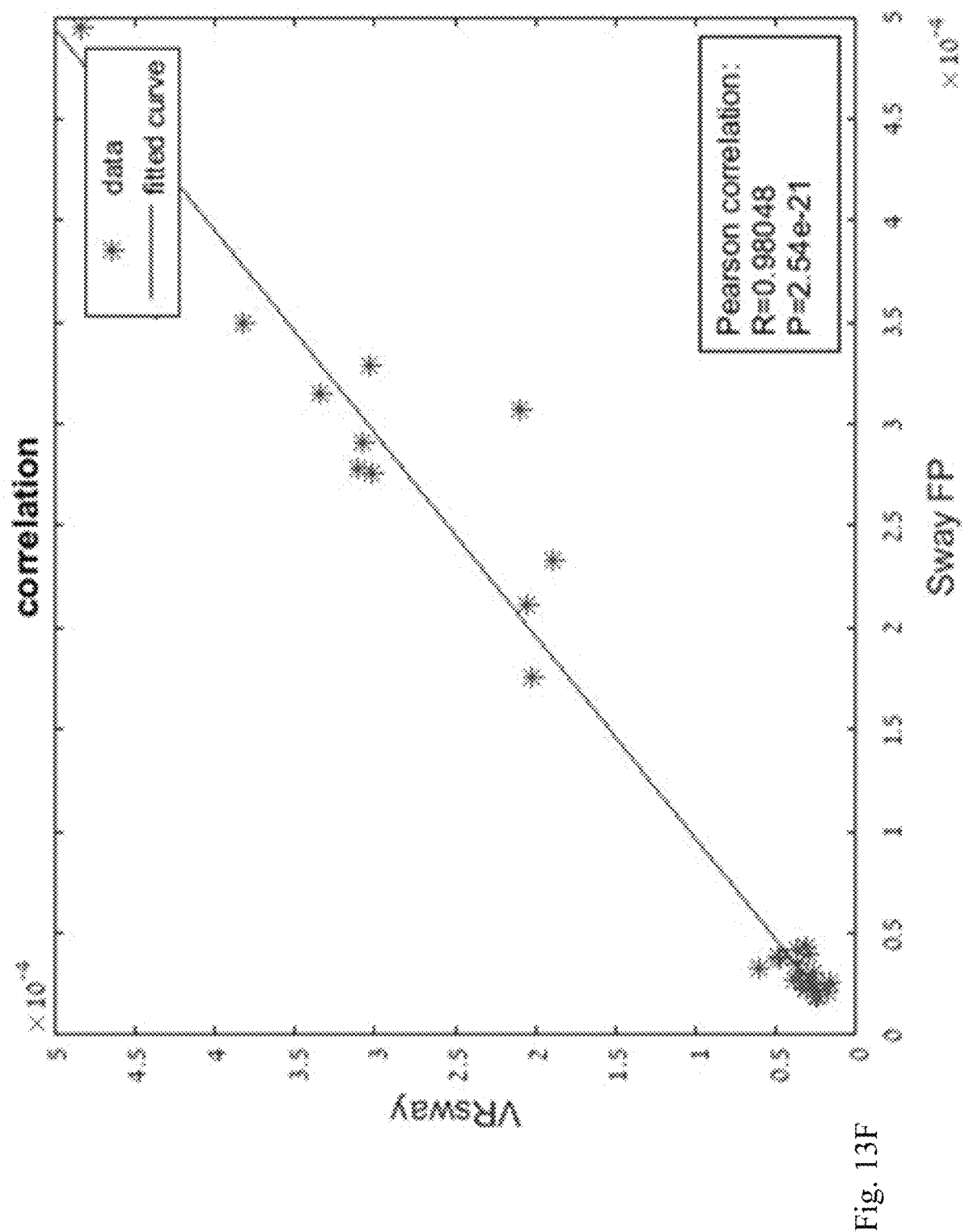

Referring to FIG. 5, a method of sway assessment according to embodiments of the present disclosure is illustrated. At 501, position data is collected from a user. In some embodiments, the position data is collected from sensors including those within a head mounted display or handheld controllers. In some embodiments, data is collected at a rate of up to about 150 Hz. In some embodiments, a user is provided with per-assessment guidance on which sensors are needed and in what positions (e.g., hand controllers above the waist). In some embodiments, a user is provided with guidance as to the precise postural position of the patient (e.g., tandem standing).

At 502, the positional data is processed to determine the center of mass of the user. In some embodiments, the center of mass is computed in three dimensions.

In some embodiments, the center of mass is represented by a 3-dimensional position calculated from the head mounted display and two hand sensors. This point, C, may be calculated as a weighted average of the three sensors according to Equation 1, where X, Y, Z are the coordinates of a given sensor, a, b, c are weighting constants, rhs identified the left hand sensor, lhs identifies the right hand sensor, and hmd identifies the head-mounted display.

$$C = a(X_{rhs}, Y_{rhs}, Z_{rhs}) + b(X_{lhs}, Y_{lhs}, Z_{lhs}) + c(X_{hmd}, Y_{hmd}, Z_{hmd})$$ Equation 1

In various embodiments, the constants a, b, c are determined based on individual attributes, including distance between hands and head, and distance between hands. In some embodiments, constants a, b, c are tuned by application of machine learning. In some embodiments, a, b, c are adjusted based on patient dimensions derived from stereo camera data.

In various embodiments, constants a, b, and c may be equal to one another. In various embodiments, constants a, b, and c may be different from one another. For example, constant c may be weighted more than constants a and b. In another example, constant c may be weighted more than constants a and b, and constants a and b may be equal to one another. For example, positional data from the head-mounted display may be weighted at 50% while the hand sensors (i.e., LHS and RHS) may each be weighted at 25%. The head-mounted display may provide more accurate positional data than the hand sensors, and thus be weighted more than the hand sensors, if, for example, patients have a tendency to move their hands excessively during postural sway evaluation.

In addition to the center of gravity, the head sway index (HSI) and torso sway index (TSI) may be computed and stored at regular intervals. The head sway index is computed from $X_{hmd}$, $Y_{hmd}$, $Z_{hmd}$, representing the coordinates of the head-mounted display. The torso sway index is computed from $X_{rhs}$, $Y_{rhs}$, $Z_{rhs}$ and $X_{lhs}$, $Y_{lhs}$, $Z_{lhs}$, representing the coordinates of the extremities.

In various embodiments, a sway index may be computed using only X and Y parameters of the recorded positional data. An average X value may be computed as $\overline{X}$ from the recorded X positions and an average Y value may be computed as $\overline{Y}$ from the recorded Y positions. The sway index may be calculated according to:

$$\text{Sway Index} = \frac{\sqrt{\sum_{n=0}^{N-1}\left((X_n - \overline{X})^2 + (Y_n - \overline{Y})^2\right)}}{n}$$ Equation 2

At 503, the raw position data and center of mass are sent to a remote server. At the server, additional analysis may be conducted. In some embodiments, the raw positional data may be filtered by any suitable filter as is known in the art. For example, a convolutional smoothing filter may be applied to the raw positional data. In some embodiments, the raw positional data may be down-sampled. For example, the raw data may be down-sampled to 20 Hz. In some embodiments, a sway index is computed.

At 504, a report of user sway is generated based on the center of mass over time. In some embodiments, the report is sent to the user via a network.

In this way, systems according to the present disclosure are continuously calculating the patient's center of mass using a smart algorithm and giving the patient instruction in a VR environment about his posture during the test. The center of mass of the patient is saved at up to 150 Hz on a server, enabling the calculation of different sway indexes (e.g., sway index or stability index). A 3-dimensional dynamic result of the patient's center of mass is provided, located on average in the S2 vertebra point while standing.

A patient's balance may be challenged through a change of scenery or environment. The challenge within the VR/AR environment may include a challenge to the visual and vestibular systems in order to get a more complex and comprehensive test. For example, the vestibular system may be manipulated by changing the virtual/augmented experience by slowly rotating the horizon to effect balance. In another example, the vision system may be manipulated by changing the virtual/augmented experience by changing the light in the environment to make it harder to notice details. In another example, scenery may be adjusted during the test according to the patient sway index in real time. This enables a more precise comprehensive result regarding a patient's postural sway status.

In various embodiments, sway may be measured during different tasks. Using VR/AR allows testing of a patient's sway in different tasks and scenarios, from day to day functional scenarios to specific scenarios crafted for the sway test.

In various embodiments, off-the-shelf VR systems are optionally used with additional external compatible sensors to track various elements in multiple fields including, e.g., motion tracking, cognitive challenges, speech recognition, stability, facial expression recognition, and biofeedback.

Motion tracking can include, but is not limited to tracking of gait, stability, tremors, amplitude of motion, speed of motion, range of motion, and movement analysis (smoothness, rigidity, etc.).

Cognitive challenges can include, but are not limited to reaction time, success rate in cognitive challenges, task fulfillment according to different kind of guidance (verbal, written, illustrated, etc.), understanding instructions, memory challenges, social interaction, and problem solving.

Speech Recognition can include, but is not limited to fluent speech, ability to imitate, and pronunciation.

Stability can include, but is not limited to postural sway.

Bio-Feedback can include, but is not limited to, Heart rate variability (HRV), Electrothermal activity (EDA), Galvanic skin response (GSR), Electroencephalography (EEG), Electromyography (EMG), Eye tracking, Electrooculography (EOG), Patient's range of motion (ROM), Patient's velocity performance, Patient's acceleration performance, and Patient's smoothness performance.

In various embodiments, positional data may be recorded with infrared sensors. In various embodiments, a gyroscope and/or accelerometer may be used to record positional information of a user and/or forces experienced by the user, either separately or concurrently with other sensors, such as the infrared sensors. In various embodiments, the gyroscope and/or accelerometer may be housed within a mobile electronic device, such as, for example, a mobile phone, that may be attached to the user.

Experiments were performed with two healthy subjects (having no history of balance disorders such as vertigo, disequilibrium, presyncope, etc.) to determine the effectiveness of determining postural sway using a VR system and sensors described herein against a force plate balance-measuring system. Positional data of the subjects were gathered using the VR system and a center of mass and sway index were calculated from these data. Positional data of the subjects were also gathered using the force plate balance-measuring system and a center of mass and sway index were calculated from this data. Sway indices calculated from the VR system and the force plate balance-measuring system were plotted against one another to determine correlation, as shown in FIGS. 6, 7, 8A-8F, 9A-9F, 10A-10F, 11A-11F, 12A-12F, and 13A-13F. In summary, the experiments demonstrated a strong correlation between the sway index calculated using a VR system and the sway index calculated using a force plate balance system, thus verifying the ability of the VR system to accurately measure a sway index. The sway index calculated from positional data gathered from only the head-mounted display resulted in the strongest correlation to the force plate balance-measuring system.

During the experiments, sway index was analyzed in six different conditions: (1) subject eyes open, subject on a firm surface; (2) subject eyes open, subject on a dynamic surface; (3) subject eyes closed, subject on a firm surface; (4) subject eyes closed, subject on a dynamic surface; (5) subject in an environment with visual conflict, subject on a firm surface; and (6) subject in an environment with visual conflict, subject on a dynamic surface. Condition (1) incorporates visual, vestibular, and somatosensory inputs. Condition (2) eliminates visual input to evaluate vestibular and somatosensory inputs. Condition (3) is used to evaluate somatosensory interaction with visual input. Condition (4) is used to evaluate somatosensory interaction with vestibular input. Condition (5) is used to evaluate further vestibular and somatosensory inputs as some vision is present but the visual information conflicts with vestibular information. Condition (6) is used to evaluate mediation of visual with vestibular and somatosensory inputs.

During the experiments, the subjects stood with feet apart to pelvic width, hip joints in neutral position, and feet parallel to one another. Each condition was measured for 30 seconds with conditions (1), (2), and (5) measured six times and conditions (3), (4), and (6) measured four times.

A dynamic surface may be provided via a balance pad. Visual conflict may be provided, for example, by moving the horizon displayed in the head-mounted display in a particular direction. For example, the horizon may be moved up, down, left, right, or in any suitable combination of directions either sequentially or together. In various embodiments, visual conflict may be provided by altering the environment displayed to each eye of a user. For example, one eye may be shown one environment (still or in motion) while the other eye may be shown another environment (still or in motion).

In various embodiments, because some patients may experience nausea during postural sway evaluation—for example, during conditions (5) and (6) where visual conflict is introduced—a nausea-reduction system may be implemented in the VR/AR system. When patients see or otherwise experience an accelerating frame of reference, but do not feel the acceleration in their ear, the patient may begin to feel nauseated. To address patient nausea during postural sway evaluation, in various embodiments, the patient's field of vision of the VR environment may be reduced/narrowed within the head-mounted display. For example, the field of vision may be vertically and/or horizontally reduced. A reduced/narrowed field of vision may reduce or eliminate feelings of nausea experienced by a patient during postural sway evaluation.

FIGS. 6 and 7 show tables of Pearson correlation coefficients for a first and second patient, respectively. In particular, FIGS. 6 and 7 shows the Pearson correlation coefficients for each of the following recorded and/or computed variables: Sway Index, Total Displacement of the Center of Pressure, Center of Pressure Mean Velocity, Ellipse Radius 1, Ellipse Radius 2, and Ellipse Area. Center of pressure (CoP) is the term given to the point of application of the ground reaction force vector. The ground reaction force vector represents the sum of all forces acting between a physical object and its supporting surface. The ellipse metrics described above reflect the dynamic nature of the CoP, and describe the area traversed by the CoP during testing.

Each of the above variables was recorded or computed for three different scenarios. In the first scenario (identified as HMD), only data from the head-mounted display (HMD) were used to compute the center of mass and sway index. In the second scenario (identified as HMD_HANDS), data from the head-mounted display (HMD) and the left hand sensor (LHS) and right hand sensor (RHS) were used to compute the center of mass and sway index. Equal weights were applied to each of the positional data sources (i.e., HMD, LHS, and RHS). In the third scenario (identified as HMD_HANDS_weighted), data from the head-mounted display (HMD) and the left hand sensor (LHS) and right hand sensor (RHS) were used to compute the center of mass and sway index. Different weights were applied to the positional data sources (i.e., HMD, LHS, and RHS). For example, the positional data from the HMD may be weighted at 50% while the positional data from the LHS and RHS may be weighted at 25% each.

FIGS. 8A-8F show graphs of Pearson correlations of VR and force plate methods for the first patient. In particular, FIGS. 8A-8F show the Pearson correlations of the sway index computed by the VR system using only positional data from the HMD against the sway index computed by a force plate for the first patient.

FIGS. 9A-9F show graphs of Pearson correlations of VR and force plate methods for the first patient. In particular, FIGS. 9A-9F show the Pearson correlations of the sway index computed by the VR system using positional data from the HMD, LHS, and RHS against the sway index computed by a force plate for the first patient. Equal weights were applied to each of the positional data sources (i.e., HMD, LHS, and RHS).

FIGS. 10A-10F show graphs of Pearson correlations of VR and force plate methods for the first patient. In particular, FIGS. 10A-10F show the Pearson correlations of the sway index computed by the VR system using positional data from the HMD, LHS, and RHS against the sway index computed by a force plate for the first patient. Different weights were applied to each of the positional data sources (i.e., HMD, LHS, and RHS) such that the positional data from the HMD were given a weight of 50% while the positional data for the LHS and RHS were given a weight of 25% each.

FIGS. 11A-11F shows graphs of Pearson correlations of VR and force plate methods for a second patient. In particular, FIGS. 11A-11F show the Pearson correlations of the sway index computed by the VR system using only positional data from the HMD against the sway index computed by a force plate for the first patient.

FIGS. 12A-12F shows graphs of Pearson correlations of VR and force plate methods for a second patient. In particular, FIGS. 12A-12F show the Pearson correlations of the sway index computed by the VR system using positional data from the HMD, LHS, and RHS against the sway index computed by a force plate for a second patient. Equal weights were applied to each of the positional data sources (i.e., HMD, LHS, and RHS).

FIGS. 13A-13F shows graphs of Pearson correlations of VR and force plate methods for a second patient. In particular, FIGS. 13A-13F show the Pearson correlations of the sway index computed by the VR system using positional data from the HMD, LHS, and RHS against the sway index computed by a force plate for a second patient. Different weights were applied to each of the positional data sources (i.e., HMD, LHS, and RHS) such that the positional data from the HMD were given a weight of 50% while the positional data for the LHS and RHS were given a weight of 25% each.

Figure 14:
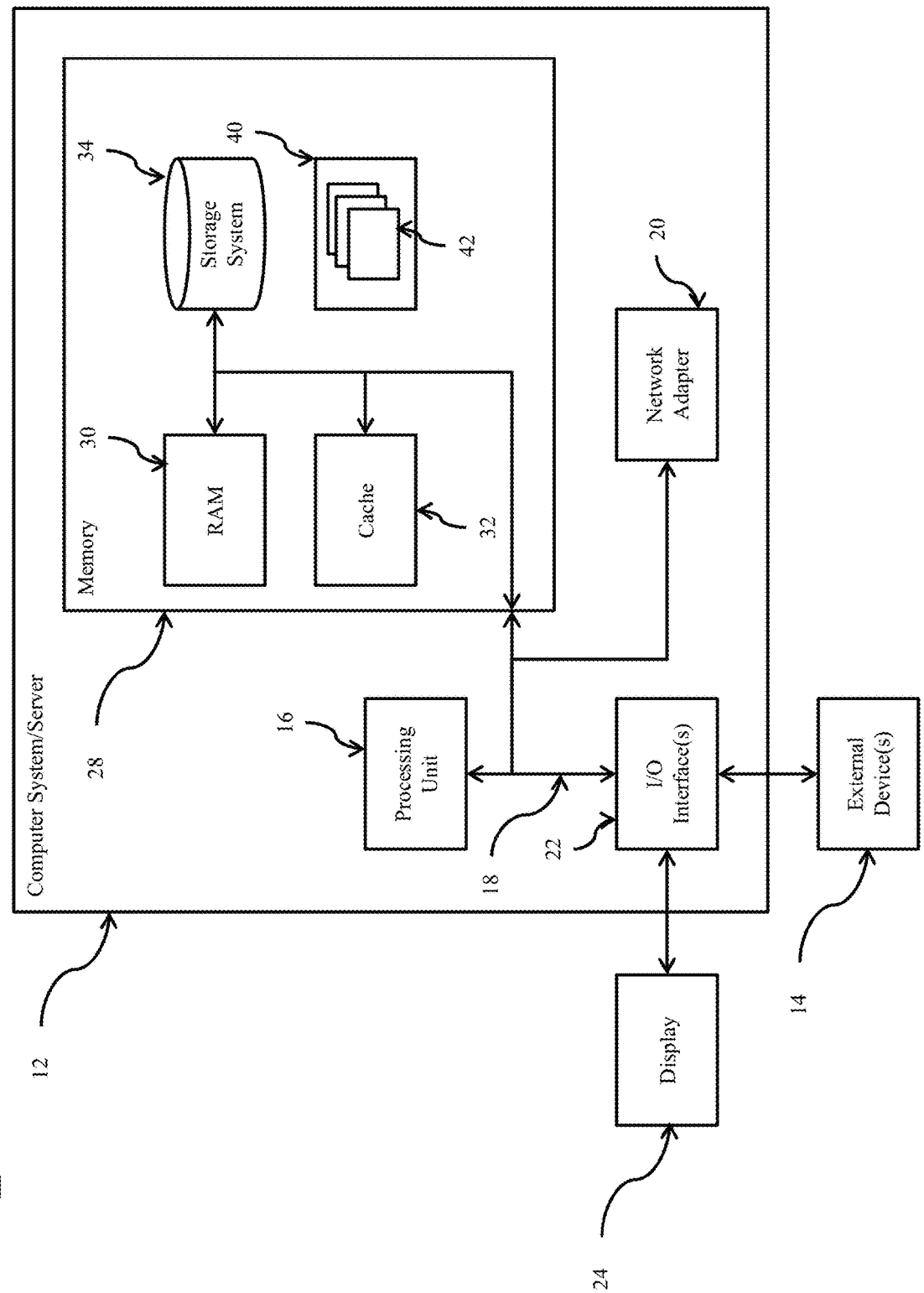
FIG. 14 depicts a computing node according to an embodiment of the present disclosure.

Referring now to FIG. 14, a schematic of an example of a computing node is shown. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 14, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Embodiments of the present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
providing a virtual environment to a user via a virtual or augmented reality system, the virtual reality system comprising a head-mounted display;
collecting positional information of the user, wherein collecting positional information comprises collecting positional information of the head-mounted display;
determining a center of mass of the user from the positional information; and determining a user sway metric from the center of mass, wherein determining the user sway metric comprises computing a standard deviation of the center of mass from a predetermined baseline.

2. The method of claim 1, wherein collecting positional information comprises collecting positional information of a first hand sensor and a second hand sensor.

3. The method of claim 1, further comprising altering the virtual environment to simulate an unbalancing of the user by moving a horizon in a predetermined direction.

4. The method of claim 3, further comprising narrowing a field of vision of the user while altering the environment.

5. The method of claim 2, wherein determining the user sway metric comprises assigning a first weight to positional information of the head mounted display, assigning a second weight to positional information of the first hand sensor, and assigning a third weight to positional information of the second hand sensor.

6. The method of claim 5, wherein the first weight, the second weight, and the third weight are equal.

7. The method of claim 5, wherein the first weight, the second weight, and the third weight are different.

8. The method of claim 5, wherein the first weight is greater than the second weight and the third weight.

9. A system comprising:
a virtual or augmented reality display adapted to display a virtual environment to a user, the virtual reality display comprising a head-mounted display;
a computing node comprising a computer readable storage medium having program instructions embodied therewith, the program instructions executable by a processor of the computing node to cause the processor to perform a method comprising:
collecting positional information of the user, wherein collecting positional information comprises collecting positional information of the head-mounted display;
determining a center of mass of the user from the positional information; and
determining a user sway metric from the center of mass, wherein determining the user sway metric comprises computing a standard deviation of the center of mass from a predetermined baseline.

10. The system of claim 9, the system further comprising a first hand sensor and a second hand sensor, wherein collecting positional information comprises collecting positional information of the first hand sensor and the second hand sensor.

11. A computer program product for assessing postural sway, the computer program product comprising a computer readable storage medium having program instructions embodied therewith, the program instructions executable by a processor to cause the processor to perform a method comprising:
collecting positional information of a user, wherein collecting positional information comprises collecting positional information of the head-mounted display;
determining a center of mass of the user from the positional information; and
determining a user sway metric from the center of mass, wherein determining the user sway metric comprises computing a standard deviation of the center of mass from a predetermined baseline.

12. The computer program product of claim 11, wherein collecting positional information comprises collecting positional information of a first hand sensor and a second hand sensor.

13. The computer program product of claim 11, the program instructions further executable by the processor to alter the virtual environment to simulate an unbalancing of the user by moving a horizon in a predetermined direction.

14. The computer program product of claim 13, the program instructions further executable by the processor to narrow a field of vision of the user while altering the environment.

15. The computer program product of claim 12, wherein determining the user sway metric comprises assigning a first weight to positional information of the head mounted display, assigning a second weight to positional information of the first hand sensor, and assigning a third weight to positional information of the second hand sensor.

16. The computer program product of claim 15, wherein the first weight, the second weight, and the third weight are equal.

17. The computer program product of claim 15, wherein the first weight, the second weight, and the third weight are different.

18. The computer program product of claim 15, wherein the first weight is greater than the second weight and the third weight.

* * * * *